United States Patent [19]
Vinkemeier et al.

[11] Patent Number: 6,087,478
[45] Date of Patent: Jul. 11, 2000

[54] CRYSTAL OF THE N-TERMINAL DOMAIN OF A STAT PROTEIN AND METHODS OF USE THEREOF

[75] Inventors: Uwe Vinkemeier, New York, N.Y.; Ismail Moarefi, Martinsried, Germany; James E. Darnell, Jr., Larchmont; John Kuriyan, Riverdale, both of N.Y.

[73] Assignee: The Rockefeller University, New York, N.Y.

[21] Appl. No.: 09/012,710

[22] Filed: Jan. 23, 1998

[51] Int. Cl.[7] .................................................... C07K 1/00
[52] U.S. Cl. .................... 530/350; 530/421; 435/69.1; 436/86; 702/19
[58] Field of Search .................................... 530/350, 421; 536/23.5; 435/252.33, 320.1, 69.1; 436/86; 702/19

[56] References Cited

FOREIGN PATENT DOCUMENTS

WO 93/19179  9/1993  WIPO.
WO 95/08629  3/1995  WIPO.

OTHER PUBLICATIONS

Vinkemeier et al. "Structure of the amino terminal protein interaction domain of STAT–4" Science, 279, 1048–1052, Feb. 1998.
Becker et al. "Three–dimentional structure of the stat3beta homodimer bound to DNA" Nature, 394, 145–151, Jul. 1998.
Chen et al. "Crystal structure of a tyrosine phosphorylated STAT–1 dimer bound to DNA" Cell, 93, 827–839, May 1998.
Kawata et al, 1997, Cell, 89:909.
Leung et al, 1995, Mol Cell Biol, 15:1312.
McKnight, 1996, Genes & Development, 10:367.
Muller et al, 1993, EMBO J, 12:4221.
Nicholls eet al, 1991, Proteins: Struct Funct ad Genetics, 11:281.
Schindler et al, 1995, Annu Rev Biochem, 64:621.
Shuai et al, 1996, Mol Cell Biol, 16:4932.
Tijan et al, 1994, Cell, 77:5.
Vinkemeier et al, 1996, EMBO J, 15:5616.
Wagner et al, 1990, EMBO J, 9:4477.
Xu et al, 1996, Science, 273:794.
Yan et al, 1996, Proc Natl Acad Sci USA, 93:5842.
Zhang et al, 1996, Proc Natl Acad Sci USA, 93:15092.
Bugg et al, 1993, Scientific American, Dec.:92–8.
Carson 1991, J Appl Cryst, 24:958.
Darnell et al, 1994, Science, 264:1415.
Darnell et al, 1997, PNAS, 94: 11767–9.
Hendrickson, 1991, Science., 254:51–58.
Horvath et al, 1995, Genes & Devel, 9:984.
Hou et al, 1996, Cell, 84:411.
Jones et al, 1991, Acta Cryst, A47:110–119.

*Primary Examiner*—Nashaat Nashed
*Attorney, Agent, or Firm*—Klauber & Jackson

[57] ABSTRACT

The present invention provides a crystal containing the N-terminal domain of a STAT protein that is of sufficient quality to perform X-ray crystallographic studies. Methods of preparing the crystals are include in the invention. The present invention further discloses the three-dimensional structure of the crystal. The present invention also provides methods of using the structural information in drug discovery and drug development.

5 Claims, 6 Drawing Sheets

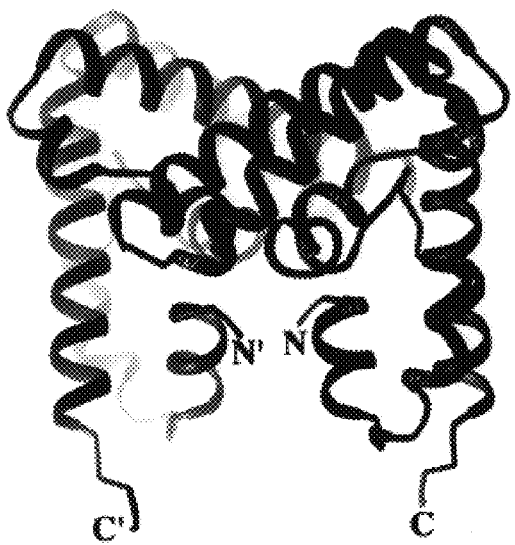
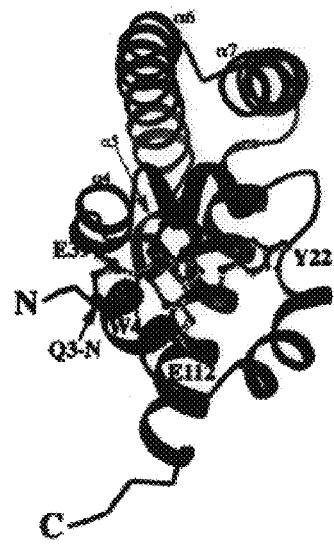

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:1:

```
Arg Xaa Xaa Leu Xaa Xaa Trp Xaa Glu Xaa Gln Xaa Trp
1               5                   10
```

(2) INFORMATION FOR SEQ ID NO:2:

(i) SEQUENCE CHARACTERISTICS:
        (A) LENGTH: 851 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:2:

```
Met Ala Gln Trp Glu Met Leu Gln Asn Leu Asp Ser Pro Phe Gln Asp
1               5                   10                  15

Gln Leu His Gln Leu Tyr Ser His Ser Leu Leu Pro Val Asp Ile Arg
                20                  25                  30

Gln Tyr Leu Ala Val Trp Ile Glu Asp Gln Asn Trp Gln Glu Ala Ala
            35                  40                  45

Leu Gly Ser Asp Asp Ser Lys Ala Thr Met Leu Phe Phe His Phe Leu
        50                  55                  60

Asp Gln Leu Asn Tyr Glu Cys Gly Arg Cys Ser Gln Asp Pro Glu Ser
65                  70                  75                  80

Leu Leu Leu Gln His Asn Leu Arg Lys Phe Cys Arg Asp Ile Gln Pro
                85                  90                  95

Phe Ser Gln Asp Pro Thr Gln Leu Ala Glu Met Ile Phe Asn Leu Leu
            100                 105                 110

Leu Glu Glu Lys Arg Ile Leu Ile Gln Ala Gln Arg Ala Gln Leu Glu
        115                 120                 125

Gln Gly Glu Pro Val Leu Glu Thr Pro Val Glu Ser Gln Gln His Glu
130                 135                 140

Ile Glu Ser Arg Ile Leu Asp Leu Arg Ala Met Met Glu Lys Leu Val
145                 150                 155                 160

Lys Ser Ile Ser Gln Leu Lys Asp Gln Gln Asp Val Phe Cys Phe Arg
                165                 170                 175

Tyr Lys Ile Gln Ala Lys Gly Lys Thr Pro Ser Leu Asp Pro His Gln
            180                 185                 190

Thr Lys Glu Gln Lys Ile Leu Gln Glu Thr Leu Asn Glu Leu Asp Lys
        195                 200                 205

Arg Arg Lys Glu Val Leu Asp Ala Ser Lys Ala Leu Leu Gly Arg Leu
210                 215                 220

Thr Thr Leu Ile Glu Leu Leu Leu Pro Lys Leu Glu Glu Trp Lys Ala
225                 230                 235                 240

Gln Gln Gln Lys Ala Cys Ile Arg Ala Pro Ile Asp His Gly Leu Glu
                245                 250                 255
```

```
Gln Leu Glu Thr Trp Phe Thr Ala Gly Ala Lys Leu Leu Phe His Leu
                260                 265                 270
Arg Gln Leu Leu Lys Glu Leu Lys Gly Leu Ser Cys Leu Val Ser Tyr
            275                 280                 285
Gln Asp Asp Pro Leu Thr Lys Gly Val Asp Leu Arg Asn Ala Gln Val
        290                 295                 300
Thr Glu Leu Leu Gln Arg Leu Leu His Arg Ala Phe Val Val Glu Thr
305                 310                 315                 320
Gln Pro Cys Met Pro Gln Thr Pro His Arg Pro Leu Ile Leu Lys Thr
                325                 330                 335
Gly Ser Lys Phe Thr Val Arg Thr Arg Leu Leu Val Arg Leu Gln Glu
            340                 345                 350
Gly Asn Glu Ser Leu Thr Val Glu Val Ser Ile Asp Arg Asn Pro Pro
        355                 360                 365
Gln Leu Gln Gly Phe Arg Lys Phe Asn Ile Leu Thr Ser Asn Gln Lys
        370                 375                 380
Thr Leu Thr Pro Glu Lys Gly Gln Ser Gln Gly Leu Ile Trp Asp Phe
385                 390                 395                 400
Gly Tyr Leu Thr Leu Val Glu Gln Arg Ser Gly Ser Gly Lys Gly
                405                 410                 415
Ser Asn Lys Gly Pro Leu Gly Val Thr Glu Leu His Ile Ile Ser
                420                 425                 430
Phe Thr Val Lys Tyr Thr Tyr Gln Gly Leu Lys Gln Glu Leu Lys Thr
                435                 440                 445
Asp Thr Leu Pro Val Val Ile Ile Ser Asn Met Asn Gln Leu Ser Ile
        450                 455                 460
Ala Trp Ala Ser Val Leu Trp Phe Asn Leu Leu Ser Pro Asn Leu Gln
465                 470                 475                 480
Asn Gln Gln Phe Phe Ser Asn Pro Pro Lys Ala Pro Trp Ser Leu Leu
                485                 490                 495
Gly Pro Ala Leu Ser Trp Gln Phe Ser Ser Tyr Val Gly Arg Gly Leu
            500                 505                 510
Asn Ser Asp Gln Leu Ser Met Leu Arg Asn Lys Leu Phe Gly Gln Asn
        515                 520                 525
Cys Arg Thr Glu Asp Pro Leu Leu Ser Trp Ala Asp Phe Thr Lys Arg
530                 535                 540
Glu Ser Pro Pro Gly Lys Leu Pro Phe Trp Thr Trp Leu Asp Lys Ile
545                 550                 555                 560
Leu Glu Leu Val His Asp His Leu Lys Asp Leu Trp Asn Asp Gly Arg
                565                 570                 575
Ile Met Gly Phe Val Ser Arg Ser Gln Glu Arg Arg Leu Leu Lys Lys
            580                 585                 590
Thr Met Ser Gly Thr Phe Leu Leu Arg Phe Ser Glu Ser Ser Glu Gly
        595                 600                 605
Gly Ile Thr Cys Ser Trp Val Glu His Gln Asp Asp Asp Lys Val Leu
        610                 615                 620
Ile Tyr Ser Val Gln Pro Tyr Thr Lys Glu Val Leu Gln Ser Leu Pro
625                 630                 635                 640
Leu Thr Glu Ile Ile Arg His Tyr Gln Leu Leu Thr Glu Glu Asn Ile
                645                 650                 655
Pro Glu Asn Pro Leu Arg Phe Leu Tyr Pro Arg Ile Pro Arg Asp Glu
            660                 665                 670
```

```
Ala Phe Gly Cys Tyr Tyr Gln Glu Lys Val Asn Leu Gln Glu Arg Arg
            675                 680                 685

Lys Tyr Leu Lys His Arg Leu Ile Val Val Ser Asn Arg Gln Val Asp
        690                 695                 700

Glu Leu Gln Gln Pro Leu Glu Leu Lys Pro Glu Pro Glu Leu Glu Ser
705                 710                 715                 720

Leu Glu Leu Glu Leu Gly Leu Val Pro Glu Pro Glu Leu Ser Leu Asp
                725                 730                 735

Leu Glu Pro Leu Leu Lys Ala Gly Leu Asp Leu Gly Pro Glu Leu Glu
                740                 745                 750

Ser Val Leu Glu Ser Thr Leu Glu Pro Val Ile Glu Pro Thr Leu Cys
                755                 760                 765

Met Val Ser Gln Thr Val Pro Glu Pro Asp Gln Gly Pro Val Ser Gln
            770                 775                 780

Pro Val Pro Glu Pro Asp Leu Pro Cys Asp Leu Arg His Leu Asn Thr
785                 790                 795                 800

Glu Pro Met Glu Ile Phe Arg Asn Cys Val Lys Ile Glu Glu Ile Met
                805                 810                 815

Pro Asn Gly Asp Pro Leu Leu Ala Gly Gln Asn Thr Val Asp Glu Val
                820                 825                 830

Tyr Val Ser Arg Pro Ser His Phe Tyr Thr Asp Gly Pro Leu Met Pro
                835                 840                 845

Ser Asp Phe
    850

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:3:

Gly Ser Gly Gly Gly
1               5

(2) INFORMATION FOR SEQ ID NO:4:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "PRIMER"

(iii) HYPOTHETICAL: NO (xi) SEQUENCE DESCRIPTION: SEQ ID NO:4:

GCCAGTCAGT TCCCGTCAAT GCATCAGGTT CCCGTCAATG CAT                43

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:5:

GCCGATTTCC CGTAAATCAT                                                      20

(2) INFORMATION FOR SEQ ID NO:6:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:6:

GATCAGTTCC CGTCAATCNA TGATCCAGTT CCCGTCAATG ATCCCCGGGA TC                  52

(2) INFORMATION FOR SEQ ID NO:7:

(i) SEQUENCE CHARACTERISTICS:
        (A) LENGTH: 749 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:7:

Met Ser Gln Trp Phe Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Tyr
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Val Gln Met Ser Met Ile Ile Tyr Asn Cys Leu Lys Glu Glu
            100                 105                 110

Arg Lys Ile Leu Glu Asn Ala Gln Arg Phe Asn Gln Ala Gln Glu Gly
        115                 120                 125

Asn Ile Gln Asn Thr Val Met Leu Asp Lys Gln Lys Glu Leu Asp Ser
    130                 135                 140

Lys Val Arg Asn Val Lys Asp Gln Val Met Cys Ile Glu Gln Glu Ile
145                 150                 155                 160

Lys Thr Leu Glu Glu Leu Gln Asp Glu Tyr Asp Phe Lys Cys Lys Thr
                165                 170                 175

Ser Gln Asn Arg Glu Gly Glu Ala Asn Gly Val Ala Lys Ser Asp Gln
            180                 185                 190

-continued

```
Lys Gln Glu Gln Leu Leu Leu His Lys Met Phe Leu Met Leu Asp Asn
            195                 200                 205

Lys Arg Lys Glu Ile Ile His Lys Ile Arg Glu Leu Leu Asn Ser Ile
210                 215                 220

Glu Leu Thr Gln Asn Thr Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
            245                 250                 255

Asp Gln Leu Gln Thr Trp Phe Thr Ile Val Ala Glu Thr Leu Gln Gln
            260                 265                 270

Ile Arg Gln Gln Leu Lys Lys Leu Glu Glu Leu Glu Gln Lys Phe Thr
            275                 280                 285

Tyr Glu Pro Asp Pro Ile Thr Lys Asn Lys Gln Val Leu Ser Asp Arg
            290                 295                 300

Thr Phe Leu Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
            325                 330                 335

Thr Gly Val Gln Phe Thr Val Lys Ser Arg Leu Leu Val Lys Leu Gln
            340                 345                 350

Glu Ser Asn Leu Leu Thr Lys Val Lys Cys His Phe Asp Lys Asp Val
            355                 360                 365

Asn Glu Lys Asn Thr Val Lys Gly Phe Arg Lys Phe Asn Ile Leu Gly
            370                 375                 380

Thr His Thr Lys Val Met Asn Met Glu Glu Ser Thr Asn Gly Ser Leu
385                 390                 395                 400

Ala Ala Glu Leu Arg His Leu Gln Leu Lys Glu Gln Lys Asn Ala Gly
            405                 410                 415

Asn Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
            435                 440                 445

Glu Thr Thr Ser Leu Pro Val Val Val Ile Ser Asn Val Ser Gln Leu
450                 455                 460

Pro Ser Gly Trp Ala Ser Ile Leu Trp Tyr Asn Met Leu Val Thr Glu
465                 470                 475                 480

Pro Arg Asn Leu Ser Phe Phe Leu Asn Pro Pro Cys Ala Trp Trp Ser
            485                 490                 495

Gln Leu Ser Glu Val Leu Ser Trp Gln Phe Ser Ser Val Thr Lys Arg
            500                 505                 510

Gly Leu Asn Ala Asp Gln Leu Ser Met Leu Gly Glu Lys Leu Leu Gly
            515                 520                 525

Pro Asn Ala Gly Pro Asp Gly Leu Ile Pro Trp Thr Arg Phe Cys Lys
            530                 535                 540

Glu Asn Ile Asn Asp Lys Asn Phe Ser Phe Trp Pro Trp Ile Asp Thr
545                 550                 555                 560

Ile Leu Glu Leu Ile Lys Asn Asp Leu Leu Cys Leu Trp Asn Asp Gly
            565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
            595                 600                 605
```

-continued

```
Glu Gly Ala Ile Thr Phe Thr Trp Val Glu Arg Ser Gln Asn Gly Gly
    610                 615                 620
Glu Pro Asp Phe His Ala Val Glu Pro Tyr Thr Lys Lys Glu Leu Ser
625                 630                 635                 640
Ala Val Thr Phe Pro Asp Ile Ile Arg Asn Tyr Lys Val Met Ala Ala
                645                 650                 655
Glu Asn Ile Pro Glu Asn Pro Leu Lys Tyr Leu Tyr Pro Asn Ile Asp
            660                 665                 670
Lys Asp His Ala Phe Gly Lys Tyr Tyr Ser Arg Pro Lys Glu Ala Pro
        675                 680                 685
Glu Pro Met Glu Leu Asp Asp Pro Lys Arg Thr Gly Tyr Ile Lys Thr
    690                 695                 700
Glu Leu Ile Ser Val Ser Glu Val His Pro Ser Arg Leu Gln Thr Thr
705                 710                 715                 720
Asp Asn Leu Leu Pro Met Ser Pro Glu Glu Phe Asp Glu Met Ser Arg
                725                 730                 735
Ile Val Gly Pro Glu Phe Asp Ser Met Met Ser Thr Val
            740                 745
```

(2) INFORMATION FOR SEQ ID NO:8:

(i) SEQUENCE CHARACTERISTICS:
        (A) LENGTH: 770 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:8:

```
Met Ala Gln Trp Asn Gln Leu Gln Gln Leu Asp Thr Arg Tyr Leu Lys
1               5                   10                  15
Gln Leu His Gln Leu Tyr Ser Asp Thr Phe Pro Met Glu Leu Arg Gln
                20                  25                  30
Phe Leu Ala Pro Trp Ile Glu Ser Gln Asp Trp Ala Tyr Ala Ala Ser
            35                  40                  45
Lys Glu Ser His Ala Thr Leu Val Phe His Asn Leu Leu Gly Glu Ile
50                  55                  60
Asp Gln Gln Tyr Ser Arg Phe Leu Gln Glu Ser Asn Val Leu Tyr Gln
65                  70                  75                  80
His Asn Leu Arg Arg Ile Lys Gln Phe Leu Gln Ser Arg Tyr Leu Glu
                85                  90                  95
Lys Pro Met Glu Ile Ala Arg Ile Val Ala Arg Cys Leu Trp Glu Glu
                100                 105                 110
Ser Arg Leu Leu Gln Thr Ala Ala Thr Ala Ala Gln Gln Gly Gly Gln
            115                 120                 125
Ala Asn His Pro Thr Ala Ala Val Val Thr Glu Lys Gln Gln Met Leu
130                 135                 140
Glu Gln His Leu Gln Asp Val Arg Lys Arg Val Gln Asp Leu Glu Gln
145                 150                 155                 160
Lys Met Lys Val Val Glu Asn Leu Gln Asp Asp Phe Asp Phe Asn Tyr
                165                 170                 175
Lys Thr Leu Lys Ser Gln Gly Asp Met Gln Asp Leu Asn Gly Asn Asn
            180                 185                 190
Gln Ser Val Thr Arg Gln Lys Met Gln Gln Leu Glu Gln Met Leu Thr
```

-continued

```
            195                 200                 205
Ala Leu Asp Gln Met Arg Arg Ser Ile Val Ser Glu Leu Ala Gly Leu
    210                 215                 220
Leu Ser Ala Met Glu Tyr Val Gln Lys Thr Leu Thr Asp Glu Glu Leu
225                 230                 235                 240
Ala Asp Trp Lys Arg Arg Gln Gln Ile Ala Cys Ile Gly Gly Pro Pro
                245                 250                 255
Asn Ile Cys Leu Asp Arg Leu Glu Asn Trp Ile Thr Ser Leu Ala Glu
            260                 265                 270
Ser Gln Leu Gln Thr Arg Gln Gln Ile Lys Lys Leu Glu Glu Leu Gln
        275                 280                 285
Gln Lys Val Ser Tyr Lys Gly Asp Pro Ile Val Gln His Arg Pro Met
    290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
            340                 345                 350
Val Lys Phe Pro Glu Leu Asn Tyr Gln Leu Lys Ile Lys Val Cys Ile
        355                 360                 365
Asp Lys Asp Ser Gly Asp Val Ala Ala Leu Arg Gly Ser Arg Lys Phe
    370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
Arg Cys Gly Asn Gly Gly Arg Ala Asn Cys Asp Ala Ser Leu Ile Val
            420                 425                 430
Thr Glu Glu Leu His Leu Ile Thr Phe Glu Thr Glu Val Tyr His Gln
        435                 440                 445
Gly Leu Lys Ile Asp Leu Glu Thr His Ser Leu Pro Val Val Val Ile
    450                 455                 460
Ser Asn Ile Cys Gln Met Pro Asn Ala Trp Ala Ser Ile Leu Trp Tyr
465                 470                 475                 480
Asn Met Leu Thr Asn Asn Pro Lys Asn Val Asn Phe Phe Thr Lys Pro
                485                 490                 495
Pro Ile Gly Thr Trp Asp Gln Val Ala Glu Val Leu Ser Trp Gln Phe
            500                 505                 510
Ser Ser Thr Thr Lys Arg Gly Leu Ser Ile Glu Gln Leu Thr Thr Leu
        515                 520                 525
Ala Glu Lys Leu Leu Gly Pro Gly Val Asn Tyr Ser Gly Cys Gln Ile
    530                 535                 540
Thr Trp Ala Lys Phe Cys Lys Glu Asn Met Ala Gly Lys Gly Phe Ser
545                 550                 555                 560
Phe Trp Val Trp Leu Asp Asn Ile Ile Asp Leu Val Lys Lys Tyr Ile
                565                 570                 575
Leu Ala Leu Trp Asn Glu Gly Tyr Ile Met Gly Phe Ile Ser Lys Glu
            580                 585                 590
Arg Glu Arg Ala Ile Leu Ser Thr Lys Pro Pro Gly Thr Phe Leu Leu
        595                 600                 605
Arg Phe Ser Glu Ser Ser Lys Glu Gly Gly Val Thr Phe Thr Trp Val
    610                 615                 620
```

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
            645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
            675                 680                 685

Pro Glu Ser Gln Glu His Pro Glu Ala Asp Pro Gly Ser Ala Ala Pro
            690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
            725                 730                 735

Phe Gly Asn Asn Gly Glu Gly Ala Glu Pro Ser Ala Gly Gly Gln Phe
            740                 745                 750

Glu Ser Leu Thr Phe Asp Met Asp Leu Thr Ser Glu Cys Ala Thr Ser
            755                 760                 765

Pro Met
    770

(2) INFORMATION FOR SEQ ID NO:9:

(i) SEQUENCE CHARACTERISTICS:
        (A) LENGTH: 749 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:9:

Met Ser Gln Trp Asn Gln Val Gln Gln Leu Glu Ile Lys Phe Leu Glu
1               5                   10                  15

Gln Val Asp Gln Phe Tyr Asp Asp Asn Phe Pro Met Glu Ile Arg His
            20                  25                  30

Leu Leu Ala Gln Trp Ile Glu Thr Gln Asp Trp Glu Val Ala Ser Asn
            35                  40                  45

Asn Glu Thr Met Ala Thr Ile Leu Leu Gln Asn Leu Leu Ile Gln Leu
            50                  55                  60

Asp Glu Gln Leu Gly Arg Val Ser Lys Glu Lys Asn Leu Leu Leu Ile
65                  70                  75                  80

His Asn Leu Lys Arg Ile Arg Lys Val Leu Gln Gly Lys Phe His Gly
            85                  90                  95

Asn Pro Met His Val Ala Val Val Ile Ser Asn Cys Leu Arg Glu Glu
            100                 105                 110

Arg Arg Ile Leu Ala Ala Ala Asn Met Pro Ile Gln Gly Pro Leu Glu
            115                 120                 125

Lys Ser Leu Gln Ser Ser Ser Val Ser Glu Arg Gln Arg Asn Val Glu
            130                 135                 140

His Lys Val Ser Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
            165                 170                 175

-continued

```
Thr Ile Gln Thr Met Asp Gln Gly Asp Lys Asn Ser Ile Leu Val Asn
            180                 185                 190

Gln Glu Val Leu Thr Leu Leu Gln Glu Met Leu Asn Ser Leu Asp Phe
            195                 200                 205

Lys Arg Lys Glu Ala Leu Ser Lys Met Thr Gln Ile Val Asn Glu Thr
            210                 215                 220

Asp Leu Leu Met Asn Ser Met Leu Leu Glu Glu Leu Gln Asp Trp Lys
225                 230                 235                 240

Lys Arg Gln Gln Ile Ala Cys Ile Gly Gly Pro Leu His Asn Gly Leu
                245                 250                 255

Asp Gln Leu Gln Asn Cys Phe Thr Leu Leu Ala Glu Ser Leu Phe Gln
            260                 265                 270

Leu Arg Gln Gln Leu Glu Lys Leu Gln Glu Gln Ser Thr Lys Met Thr
            275                 280                 285

Tyr Glu Gly Asp Pro Ile Pro Ala Gln Arg Ala His Leu Leu Glu Arg
            290                 295                 300

Ala Thr Phe Leu Ile Tyr Asn Leu Phe Lys Asn Ser Phe Val Val Glu
305                 310                 315                 320

Arg Gln Pro Cys Met Pro Thr His Pro Gln Arg Pro Met Val Leu Lys
                325                 330                 335

Thr Leu Ile Gln Phe Thr Val Lys Leu Arg Leu Leu Ile Lys Leu Pro
            340                 345                 350

Glu Leu Asn Tyr Gln Val Lys Val Lys Ala Ser Ile Asp Lys Asn Val
            355                 360                 365

Ser Thr Leu Ser Asn Arg Arg Phe Val Leu Cys Gly Thr His Val Lys
            370                 375                 380

Ala Met Ser Ser Glu Glu Ser Ser Asn Gly Ser Leu Ser Val Glu Phe
385                 390                 395                 400

Arg His Leu Gln Pro Lys Glu Met Lys Cys Ser Thr Gly Ser Lys Gly
                405                 410                 415

Asn Glu Gly Cys His Met Val Thr Glu Glu Leu His Ser Ile Thr Phe
            420                 425                 430

Glu Thr Gln Ile Cys Leu Tyr Gly Leu Thr Ile Asn Leu Glu Thr Ser
            435                 440                 445

Ser Leu Pro Val Val Met Ile Ser Asn Val Ser Gln Leu Pro Asn Ala
            450                 455                 460

Trp Ala Ser Ile Ile Trp Tyr Asn Val Ser Thr Asn Asp Ser Gln Asn
465                 470                 475                 480

Leu Val Phe Phe Asn Asn Pro Pro Ser Val Thr Leu Gly Gln Leu Leu
                485                 490                 495

Glu Val Met Ser Trp Gln Phe Ser Ser Tyr Val Gly Arg Gly Leu Asn
            500                 505                 510

Ser Glu Gln Leu Asn Met Leu Ala Glu Lys Leu Thr Val Gln Ser Asn
            515                 520                 525

Tyr Asn Asp Gly His Leu Thr Trp Ala Lys Phe Cys Lys Glu His Leu
            530                 535                 540

Pro Gly Lys Thr Phe Thr Phe Trp Thr Trp Leu Glu Ala Ile Leu Asp
545                 550                 555                 560

Leu Ile Lys Lys His Ile Leu Pro Leu Trp Ile Asp Gly Tyr Ile Met
                565                 570                 575

Gly Phe Val Ser Lys Glu Lys Glu Arg Leu Leu Leu Lys Asp Lys Met
            580                 585                 590

Pro Gly Thr Phe Leu Leu Arg Phe Ser Glu Ser His Leu Gly Gly Ile
```

```
                    595                 600                 605
Thr Phe Thr Trp Val Asp Gln Ser Glu Asn Gly Glu Val Arg Phe His
    610                 615                 620

Ser Val Glu Pro Tyr Asn Lys Gly Arg Leu Ser Ala Leu Ala Phe Ala
625                 630                 635                 640

Asp Ile Leu Arg Asp Tyr Lys Val Ile Met Ala Glu Asn Ile Pro Glu
                645                 650                 655

Asn Pro Leu Lys Tyr Leu Tyr Pro Asp Ile Pro Lys Asp Lys Ala Phe
                660                 665                 670

Gly Lys His Tyr Ser Ser Gln Pro Cys Glu Val Ser Arg Pro Thr Glu
                675                 680                 685

Arg Gly Asp Lys Gly Tyr Val Pro Ser Val Phe Ile Pro Ile Ser Thr
    690                 695                 700

Ile Arg Ser Asp Ser Thr Glu Pro Gln Ser Pro Ser Asp Leu Leu Pro
705                 710                 715                 720

Met Ser Pro Ser Ala Tyr Ala Val Leu Arg Glu Asn Leu Ser Pro Thr
                725                 730                 735

Thr Ile Glu Thr Ala Met Asn Ser Pro Tyr Ser Ala Glu
                740                 745

(2) INFORMATION FOR SEQ ID NO:10:

(i) SEQUENCE CHARACTERISTICS:
        (A) LENGTH: 793 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:10:

Met Ala Gly Trp Ile Gln Ala Gln Gln Leu Gln Gly Asp Ala Leu Arg
1               5                   10                  15

Gln Met Gln Val Leu Tyr Gly Gln His Phe Pro Ile Glu Val Arg His
                20                  25                  30

Tyr Leu Ala Gln Trp Ile Glu Ser Gln Pro Trp Asp Ala Ile Asp Leu
            35                  40                  45

Asp Asn Pro Gln Asp Arg Gly Gln Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Asn
                85                  90                  95

Thr Tyr Asp Arg Cys Pro Met Glu Leu Val Arg Cys Ile Arg His Ile
                100                 105                 110

Leu Tyr Asn Glu Gln Arg Leu Val Arg Glu Ala Asn Asn Cys Ser Ser
                115                 120                 125

Pro Ala Gly Val Leu Val Asp Ala Met Ser Gln Lys His Leu Gln Ile
            130                 135                 140

Asn Gln Arg Phe Glu Glu Leu Arg Leu Ile Thr Gln Asp Thr Glu Asn
145                 150                 155                 160

Glu Leu Lys Lys Leu Gln Gln Thr Gln Glu Tyr Phe Ile Ile Gln Tyr
                165                 170                 175

Gln Glu Ser Leu Arg Ile Gln Ala Gln Phe Ala Gln Leu Gly Gln Leu
                180                 185                 190
```

-continued

```
Asn Pro Gln Glu Arg Met Ser Arg Glu Thr Ala Leu Gln Gln Lys Gln
        195                 200                 205
Val Ser Leu Glu Thr Trp Leu Gln Arg Glu Ala Gln Thr Leu Gln Gln
        210                 215                 220
Tyr Arg Val Glu Leu Ala Glu Lys His Gln Lys Thr Leu Gln Leu Leu
225                 230                 235                 240
Arg Lys Gln Gln Thr Ile Ile Leu Asp Asp Glu Leu Ile Gln Trp Lys
                    245                 250                 255
Arg Arg Gln Gln Leu Ala Gly Asn Gly Gly Pro Pro Glu Gly Ser Leu
            260                 265                 270
Asp Val Leu Gln Ser Trp Cys Glu Lys Leu Ala Glu Ile Ile Trp Gln
            275                 280                 285
Asn Arg Gln Gln Ile Arg Arg Ala Glu His Leu Cys Gln Gln Leu Pro
        290                 295                 300
Ile Pro Gly Pro Val Glu Met Leu Ala Glu Val Asn Ala Thr Ile
305                 310                 315                 320
Thr Asp Ile Ile Ser Ala Leu Val Thr Ser Thr Phe Ile Ile Glu Lys
                    325                 330                 335
Gln Pro Pro Gln Val Leu Lys Thr Gln Thr Lys Phe Ala Ala Thr Val
            340                 345                 350
Arg Leu Leu Val Gly Gly Lys Leu Asn Val His Met Asn Pro Pro Gln
        355                 360                 365
Val Lys Ala Thr Ile Ile Ser Glu Gln Gln Ala Lys Ser Leu Leu Lys
        370                 375                 380
Asn Glu Asn Thr Arg Asn Glu Cys Ser Gly Glu Ile Leu Asn Asn Cys
385                 390                 395                 400
Cys Val Met Glu Tyr His Gln Ala Thr Gly Thr Leu Ser Ala His Phe
                    405                 410                 415
Arg Asn Met Ser Leu Lys Arg Ile Lys Arg Ala Asp Arg Arg Gly Ala
            420                 425                 430
Glu Ser Val Thr Glu Glu Lys Phe Thr Val Leu Phe Glu Ser Gln Phe
        435                 440                 445
Ser Val Gly Ser Asn Glu Leu Val Phe Gln Val Lys Thr Leu Ser Leu
        450                 455                 460
Pro Val Val Ile Val His Gly Ser Gln Asp His Asn Ala Thr Ala
465                 470                 475                 480
Thr Val Leu Trp Asp Asn Ala Phe Ala Glu Pro Gly Arg Val Pro Phe
                    485                 490                 495
Ala Val Pro Asp Lys Val Leu Trp Pro Gln Leu Cys Glu Ala Leu Asn
            500                 505                 510
Met Lys Phe Lys Ala Glu Val Gln Ser Asn Arg Gly Leu Thr Lys Glu
        515                 520                 525
Asn Leu Val Phe Leu Ala Gln Lys Leu Phe Asn Ile Ser Ser Asn His
        530                 535                 540
Leu Glu Asp Tyr Asn Ser Met Ser Val Ser Trp Ser Gln Phe Asn Arg
545                 550                 555                 560
Glu Asn Leu Pro Gly Trp Asn Tyr Thr Phe Trp Gln Trp Phe Asp Gly
                    565                 570                 575
Val Met Glu Val Leu Lys Lys His His Lys Pro His Trp Asn Asp Gly
            580                 585                 590
Ala Ile Leu Gly Phe Val Asn Lys Gln Gln Ala His Asp Leu Leu Ile
        595                 600                 605
```

-continued

Asn Lys Pro Asp Gly Thr Phe Leu Leu Arg Phe Ser Asp Ser Glu Ile
            610                 615                 620

Gly Gly Ile Thr Ile Ala Trp Lys Phe Asp Ser Pro Asp Arg Asn Leu
625                 630                 635                 640

Trp Asn Leu Lys Pro Phe Thr Thr Arg Asp Phe Ser Ile Arg Ser Leu
                645                 650                 655

Ala Asp Arg Leu Gly Asp Leu Asn Tyr Leu Ile Tyr Val Phe Pro Asp
            660                 665                 670

Arg Pro Lys Asp Glu Val Phe Ala Lys Tyr Tyr Thr Pro Val Leu Ala
        675                 680                 685

Lys Ala Val Asp Gly Tyr Val Lys Pro Gln Ile Lys Gln Val Val Pro
    690                 695                 700

Glu Phe Val Asn Ala Ser Thr Asp Ala Gly Ala Ser Ala Thr Tyr Met
705                 710                 715                 720

Asp Gln Ala Pro Ser Pro Val Val Cys Pro Gln Pro His Tyr Asn Met
                725                 730                 735

Tyr Pro Pro Asn Pro Asp Pro Val Leu Asp Gln Asp Gly Glu Phe Asp
            740                 745                 750

Leu Asp Glu Ser Met Asp Val Ala Arg His Val Glu Glu Leu Leu Arg
        755                 760                 765

Arg Pro Met Asp Ser Leu Asp Ala Arg Leu Ser Pro Pro Ala Gly Leu
    770                 775                 780

Phe Thr Ser Ala Arg Ser Ser Leu Ser
785                 790

(2) INFORMATION FOR SEQ ID NO:11:

(i) SEQUENCE CHARACTERISTICS:
        (A) LENGTH: 786 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:11:

Met Ala Met Trp Ile Gln Ala Gln Gln Leu Gln Gly Asp Ala Leu His
1               5                   10                  15

Gln Met Gln Ala Leu Tyr Gly Gln His Phe Pro Ile Glu Val Arg His
            20                  25                  30

Tyr Leu Ser Gln Trp Ile Glu Ser Gln Ala Trp Asp Ser Ile Asp Leu
        35                  40                  45

Asp Asn Pro Gln Glu Asn Ile Lys Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Ser
                85                  90                  95

Thr Tyr Asp Arg Cys Pro Met Glu Leu Val Arg Cys Ile Arg His Ile
            100                 105                 110

Leu Tyr Asn Glu Gln Arg Leu Val Arg Glu Ala Asn Asn Gly Ser Ser
        115                 120                 125

Pro Ala Gly Ser Leu Ala Asp Ala Met Ser Gln Lys His Leu Gln Ile
    130                 135                 140

Asn Gln Thr Phe Glu Glu Leu Arg Leu Ile Thr Gln Asp Thr Glu Asn

-continued

```
               145                 150                 155                 160
        Glu Leu Lys Lys Leu Gln Gln Thr Gln Glu Tyr Phe Ile Ile Gln Tyr
                        165                 170                 175

Gln Glu Ser Leu Arg Ile Gln Ala Gln Phe Ala Gln Leu Gly Gln Leu
                        180                 185                 190

Asn Pro Gln Glu Arg Met Ser Arg Glu Thr Ala Leu Gln Gln Lys Gln
                        195                 200                 205

Val Ser Leu Glu Thr Trp Leu Gln Arg Glu Ala Gln Thr Leu Gln Gln
                210                 215                 220

Tyr Arg Val Glu Leu Ala Glu Lys His Gln Lys Thr Leu Gln Leu Leu
        225                 230                 235                 240

Arg Lys Gln Gln Thr Ile Ile Leu Asp Asp Glu Leu Ile Gln Trp Lys
                        245                 250                 255

Arg Arg Gln Gln Leu Ala Gly Asn Gly Gly Pro Pro Glu Gly Ser Leu
                        260                 265                 270

Asp Val Leu Gln Ser Trp Cys Glu Lys Leu Ala Glu Ile Ile Trp Gln
                275                 280                 285

Asn Arg Gln Gln Ile Arg Arg Ala Glu His Leu Cys Gln Gln Leu Pro
                290                 295                 300

Ile Pro Gly Pro Val Glu Glu Met Leu Ala Glu Val Asn Ala Thr Ile
        305                 310                 315                 320

Thr Asp Ile Ile Ser Ala Leu Val Thr Ser Thr Phe Ile Ile Glu Lys
                        325                 330                 335

Gln Pro Pro Gln Val Leu Lys Thr Gln Thr Lys Phe Ala Ala Thr Val
                        340                 345                 350

Arg Leu Leu Val Gly Gly Lys Leu Asn Val His Met Asn Pro Pro Gln
                355                 360                 365

Val Lys Ala Thr Ile Ile Ser Glu Gln Gln Ala Lys Ser Leu Leu Lys
                370                 375                 380

Asn Glu Asn Thr Arg Asn Asp Tyr Ser Gly Glu Ile Leu Asn Asn Cys
        385                 390                 395                 400

Cys Val Met Glu Tyr His Gln Ala Thr Gly Thr Leu Ser Ala His Phe
                        405                 410                 415

Arg Asn Met Ser Leu Lys Arg Ile Lys Arg Ser Asp Arg Arg Gly Ala
                        420                 425                 430

Gly Ser Val Thr Glu Glu Lys Phe Thr Ile Leu Phe Asp Ser Gln Phe
                        435                 440                 445

Ser Val Gly Gly Asn Glu Leu Val Phe Gln Val Lys Thr Leu Ser Leu
                450                 455                 460

Pro Val Val Val Ile Val His Gly Ser Gln Asp Asn Asn Ala Thr Ala
        465                 470                 475                 480

Thr Val Leu Trp Asp Asn Ala Phe Ala Glu Pro Gly Arg Val Pro Phe
                        485                 490                 495

Ala Val Pro Asp Lys Val Leu Trp Pro Gln Leu Cys Glu Ala Leu Asn
                        500                 505                 510

Met Lys Phe Lys Ala Glu Val Gln Ser Asn Arg Gly Leu Thr Lys Glu
                        515                 520                 525

Asn Leu Val Phe Leu Ala Gln Lys Leu Phe Asn Ile Ser Ser Asn His
                530                 535                 540

Leu Glu Asp Tyr Asn Ser Met Ser Val Ser Trp Ser Gln Phe Asn Arg
        545                 550                 555                 560

Glu Asn Leu Pro Gly Arg Asn Tyr Thr Phe Trp Gln Trp Phe Asp Gly
                        565                 570                 575
```

```
Val Met Glu Val Leu Lys Lys His Leu Lys Pro His Trp Asn Asp Gly
        580                 585                 590

Ala Ile Leu Gly Phe Val Asn Lys Gln Gln Ala His Asp Leu Leu Ile
        595                 600                 605

Asn Lys Pro Asp Gly Thr Phe Leu Leu Arg Phe Ser Asp Ser Glu Ile
        610                 615                 620

Gly Gly Ile Thr Ile Ala Trp Lys Phe Asp Ser Gln Glu Arg Met Phe
625                 630                 635                 640

Trp Asn Leu Met Pro Phe Thr Thr Arg Asp Phe Ser Ile Arg Ser Leu
            645                 650                 655

Ala Asp Arg Leu Gly Asp Leu Asn Tyr Leu Ile Tyr Val Phe Pro Asp
            660                 665                 670

Arg Pro Lys Asp Glu Val Tyr Ser Lys Tyr Tyr Thr Pro Val Pro Cys
            675                 680                 685

Glu Pro Ala Thr Ala Lys Ala Ala Asp Gly Tyr Val Lys Pro Gln Ile
            690                 695                 700

Lys Gln Val Val Pro Glu Phe Asn Ala Ser Thr Asp Ala Gly Ser
705                 710                 715                 720

Gly Ala Thr Tyr Met Asp Gln Ala Pro Ser Pro Val Val Cys Pro Gln
            725                 730                 735

Ala His Tyr Asn Met Tyr Pro Pro Asn Pro Asp Ser Val Leu Asp Thr
            740                 745                 750

Asp Gly Asp Phe Asp Leu Glu Asp Thr Met Asp Val Ala Arg Arg Val
            755                 760                 765

Glu Glu Leu Leu Gly Arg Pro Met Asp Ser Gln Trp Ile Pro His Ala
770                 775                 780

Gln Ser
785

(2) INFORMATION FOR SEQ ID NO:12:

(i) SEQUENCE CHARACTERISTICS:
        (A) LENGTH: 837 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:12:

Met Ser Leu Trp Gly Leu Ile Ser Lys Met Ser Pro Glu Lys Leu Gln
1               5                   10                  15

Arg Leu Tyr Val Asp Phe Pro Gln Arg Leu His Leu Leu Ala Asp
            20                  25                  30

Trp Leu Glu Ser Gln Pro Trp Glu Phe Leu Val Gly Ser Asp Ala Phe
            35                  40                  45

Cys Tyr Asn Met Ala Ser Ala Leu Leu Ser Ala Thr Val Gln Arg Leu
        50                  55                  60

Gln Ala Thr Ala Gly Glu Gln Gly Lys Gly Asn Ser Ile Leu Pro His
65                  70                  75                  80

Ile Ser Thr Leu Glu Ser Ile Tyr Gln Arg Asp Pro Leu Lys Leu Val
            85                  90                  95

Ala Thr Ile Arg Gln Ile Leu Gln Gly Glu Lys Lys Ala Val Ile Glu
            100                 105                 110
```

-continued

```
Glu Phe Arg His Leu Pro Gly Pro Phe His Arg Lys Gln Glu Glu Leu
            115                 120                 125
Lys Phe Thr Thr Pro Leu Gly Arg Leu His His Arg Val Arg Glu Thr
130                 135                 140
Arg Leu Leu Arg Glu Ser Leu His Leu Gly Pro Lys Thr Gly Gln Val
145                 150                 155                 160
Ser Leu Gln Asn Leu Ile Asp Pro Pro Leu Asn Gly Pro Gly Pro Ser
            165                 170                 175
Glu Asp Leu Pro Thr Ile Leu Gln Gly Thr Val Gly Asp Leu Glu Thr
            180                 185                 190
Thr Gln Pro Leu Val Leu Leu Arg Ile Gln Ile Trp Lys Arg Gln Gln
            195                 200                 205
Gln Leu Ala Gly Asn Gly Thr Pro Phe Glu Glu Ser Leu Ala Gly Leu
    210                 215                 220
Gln Glu Arg Cys Glu Ser Leu Val Glu Ile Tyr Ser Gln Leu His Gln
225                 230                 235                 240
Glu Ile Gly Ala Ala Ser Gly Glu Leu Glu Pro Lys Thr Arg Ala Ser
            245                 250                 255
Leu Ile Ser Arg Leu Asp Glu Val Leu Arg Thr Leu Val Thr Ser Ser
            260                 265                 270
Phe Leu Val Glu Lys Gln Pro Pro Gln Val Leu Lys Thr Gln Thr Lys
            275                 280                 285
Phe Gln Ala Gly Val Arg Phe Leu Leu Gly Leu Gln Phe Leu Gly Thr
    290                 295                 300
Ser Thr Lys Pro Pro Met Val Arg Ala Asp Met Val Thr Glu Lys Gln
305                 310                 315                 320
Ala Arg Glu Leu Ser Leu Ser Gln Gly Pro Gly Thr Gly Val Glu Ser
            325                 330                 335
Thr Gly Glu Ile Met Asn Asn Thr Val Pro Leu Glu Asn Ser Ile Pro
            340                 345                 350
Ser Asn Cys Cys Ser Ala Leu Phe Lys Asn Leu Leu Leu Lys Lys Ile
            355                 360                 365
Lys Arg Cys Glu Arg Lys Gly Thr Glu Ser Val Thr Glu Glu Lys Cys
    370                 375                 380
Ala Val Leu Phe Ser Thr Ser Phe Thr Leu Gly Pro Asn Lys Leu Leu
385                 390                 395                 400
Ile Gln Leu Gln Ala Leu Ser Leu Ser Leu Val Val Ile Val His Gly
            405                 410                 415
Asn Gln Asp Asn Asn Ala Lys Ala Thr Ile Leu Trp Asp Asn Ala Phe
            420                 425                 430
Ser Glu Met Asp Arg Val Pro Phe Val Val Gly Glu Arg Val Pro Trp
            435                 440                 445
Glu Lys Met Cys Glu Thr Leu Asn Leu Lys Phe Met Val Glu Val Gly
    450                 455                 460
Thr Ser Arg Gly Leu Leu Pro Glu His Phe Leu Phe Leu Ala Gln Lys
465                 470                 475                 480
Ile Phe Asn Asp Asn Ser Leu Ser Val Glu Ala Phe Gln His Arg Cys
            485                 490                 495
Val Ser Trp Ser Gln Phe Asn Lys Glu Ile Leu Leu Gly Arg Gly Phe
            500                 505                 510
Thr Phe Trp Gln Trp Phe Asp Gly Val Leu Asp Leu Thr Lys Arg Cys
            515                 520                 525
Leu Arg Ser Tyr Trp Ser Asp Arg Leu Ile Ile Gly Phe Ile Ser Lys
```

-continued

```
            530                 535                 540
Gln Tyr Val Thr Ser Leu Leu Asn Glu Pro Asp Gly Thr Phe Leu
545                 550                 555                 560

Leu Arg Phe Ser Asp Ser Glu Ile Gly Ile Thr Ile Ala His Val
                565                 570                 575

Ile Arg Gly Gln Asp Gly Ser Ser Gln Ile Glu Asn Ile Gln Pro Phe
            580                 585                 590

Ser Ala Lys Asp Leu Ser Ile Arg Ser Leu Gly Asp Arg Ile Arg Asp
            595                 600                 605

Leu Ala Gln Leu Lys Asn Leu Tyr Pro Lys Pro Lys Asp Glu Ala
            610                 615                 620

Phe Arg Ser His Tyr Lys Pro Glu Gln Met Gly Lys Asp Gly Arg Gly
625                 630                 635                 640

Tyr Val Ser Thr Thr Ile Lys Met Thr Val Glu Arg Asp Gln Pro Leu
                645                 650                 655

Pro Thr Pro Glu Pro Gln Met Pro Ala Met Val Pro Pro Tyr Asp Leu
                660                 665                 670

Gly Met Ala Pro Asp Ala Ser Met Gln Leu Ser Ser Asp Met Gly Tyr
            675                 680                 685

Pro Pro Gln Ser Ile His Ser Phe Gln Ser Leu Glu Glu Ser Met Ser
            690                 695                 700

Val Leu Pro Ser Phe Gln Glu Pro His Leu Gln Met Pro Pro Asn Met
705                 710                 715                 720

Ser Gln Ile Thr Met Pro Phe Asp Gln Pro His Pro Gln Gly Leu Leu
                725                 730                 735

Gln Cys Gln Ser Gln Glu His Ala Val Ser Ser Pro Glu Pro Met Leu
            740                 745                 750

Trp Ser Asp Val Thr Met Val Glu Asp Ser Cys Leu Thr Gln Pro Val
            755                 760                 765

Gly Gly Phe Pro Gln Gly Thr Trp Val Ser Glu Asp Met Tyr Pro Pro
            770                 775                 780

Leu Leu Pro Pro Thr Glu Gln Asp Leu Thr Lys Leu Leu Leu Glu Asn
785                 790                 795                 800

Gln Gly Glu Gly Gly Gly Ser Leu Gly Ser Gln Pro Leu Leu Lys Pro
                805                 810                 815

Ser Pro Tyr Gly Gln Ser Gly Ile Ser Leu Ser His Leu Asp Leu Arg
            820                 825                 830

Thr Asn Pro Ser Trp
            835
```

(2) INFORMATION FOR SEQ ID NO:13:

(i) SEQUENCE CHARACTERISTICS:
        (A) LENGTH: 761 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:13:

```
Met Ser Leu Trp Lys Arg Ile Ser Ser His Val Asp Cys Glu Gln Arg
1               5                   10                  15

Met Ala Ala Tyr Tyr Glu Glu Lys Gly Met Leu Glu Leu Arg Leu Cys
            20                  25                  30
```

-continued

```
Leu Ala Pro Trp Ile Glu Asp Arg Ile Met Ser Glu Gln Ile Thr Pro
             35                  40                  45

Asn Thr Thr Asp Gln Leu Glu Arg Val Ala Leu Lys Phe Asn Glu Asp
 50                  55                  60

Leu Gln Gln Lys Leu Leu Ser Thr Arg Thr Ala Ser Asp Gln Ala Leu
 65                  70                  75                  80

Lys Phe Arg Val Val Glu Leu Cys Ala Leu Ile Gln Arg Ile Ser Ala
                 85                  90                  95

Val Glu Leu Tyr Thr His Leu Arg Ser Gly Leu Gln Lys Glu Leu Gln
            100                 105                 110

Leu Val Thr Glu Lys Ser Val Ala Ala Thr Ala Gly Gln Ser Met Pro
        115                 120                 125

Leu Asn Pro Tyr Asn Met Asn Asn Thr Pro Met Val Thr Gly Tyr Met
        130                 135                 140

Val Asp Pro Ser Asp Leu Leu Ala Val Ser Asn Ser Cys Asn Pro Pro
145                 150                 155                 160

Val Val Gln Gly Ile Gly Pro Ile His Asn Val Gln Asn Thr Gly Ile
                165                 170                 175

Ala Ser Pro Ala Leu Gly Met Val Thr Pro Lys Val Glu Leu Tyr Glu
            180                 185                 190

Val Gln His Gln Ile Met Gln Ser Leu Asn Glu Phe Gly Asn Cys Ala
        195                 200                 205

Asn Ala Leu Lys Leu Leu Ala Gln Asn Tyr Ser Tyr Met Leu Asn Ser
        210                 215                 220

Thr Ser Ser Pro Asn Ala Glu Ala Ala Tyr Arg Ser Leu Ile Asp Glu
225                 230                 235                 240

Lys Ala Ala Ile Val Leu Thr Met Arg Arg Ser Phe Met Tyr Tyr Glu
                245                 250                 255

Ser Leu His Glu Met Val Ile His Glu Leu Lys Asn Trp Arg His Gln
            260                 265                 270

Gln Ala Gln Ala Gly Asn Gly Ala Pro Phe Asn Glu Gly Ser Leu Asp
        275                 280                 285

Asp Ile Gln Arg Cys Phe Glu Met Leu Glu Ser Phe Ile Ala His Met
        290                 295                 300

Leu Ala Ala Val Lys Glu Leu Met Arg Val Arg Leu Val Thr Glu Glu
305                 310                 315                 320

Pro Glu Leu Thr His Leu Leu Glu Gln Val Gln Asn Ala Gln Lys Asn
                325                 330                 335

Leu Val Cys Ser Ala Phe Ile Val Asp Lys Gln Pro Pro Gln Val Met
            340                 345                 350

Lys Thr Asn Thr Arg Phe Ala Ala Ser Val Arg Trp Leu Ile Gly Ser
        355                 360                 365

Gln Leu Gly Ile His Asn Asn Pro Pro Thr Val Glu Cys Ile Ile Met
        370                 375                 380

Ser Glu Ile Gln Ser Gln Arg Phe Val Thr Arg Asn Thr Gln Met Asp
385                 390                 395                 400

Asn Ser Ser Leu Ser Gly Gln Ser Ser Gly Glu Ile Gln Asn Ala Ser
                405                 410                 415

Ser Thr Met Glu Tyr Gln Gln Asn Asn His Val Phe Ser Ala Ser Phe
            420                 425                 430

Arg Asn Met Gln Leu Lys Lys Ile Lys Arg Ala Glu Lys Lys Gly Thr
        435                 440                 445
```

-continued

```
Glu Ser Val Met Asp Glu Lys Phe Ala Leu Phe Phe Tyr Thr Thr Thr
        450                 455                 460

Thr Val Asn Asp Phe Gln Ile Arg Val Trp Thr Leu Ser Leu Pro Val
465                 470                 475                 480

Val Val Ile Val His Gly Asn Gln Glu Pro Gln Ser Trp Ala Thr Ile
                485                 490                 495

Thr Trp Asp Asn Ala Phe Ala Glu Ile Val Arg Asp Pro Phe Met Ile
            500                 505                 510

Thr Asp Arg Val Thr Trp Ala Gln Leu Ser Val Ala Leu Asn Ile Lys
            515                 520                 525

Phe Gly Ser Cys Thr Gly Arg Ser Leu Thr Ile Asp Asn Leu Asp Phe
        530                 535                 540

Leu Tyr Glu Lys Leu Gln Arg Glu Arg Ser Glu Tyr Ile Thr Trp
545                 550                 555                 560

Asn Gln Phe Cys Lys Glu Pro Met Pro Asp Arg Ser Phe Thr Phe Trp
                565                 570                 575

Glu Trp Phe Phe Ala Ile Met Lys Leu Thr Lys Asp His Met Leu Gly
            580                 585                 590

Met Trp Lys Ala Gly Cys Ile Met Gly Phe Ile Asn Lys Thr Lys Ala
        595                 600                 605

Gln Thr Asp Leu Leu Arg Ser Val Tyr Gly Ile Gly Thr Phe Leu Leu
    610                 615                 620

Arg Phe Ser Asp Ser Glu Leu Gly Gly Val Thr Ile Ala Tyr Val Asn
625                 630                 635                 640

Glu Asn Gly Leu Val Thr Met Leu Ala Pro Trp Thr Ala Arg Asp Phe
                645                 650                 655

Gln Val Leu Asn Leu Ala Asp Arg Ile Arg Asp Leu Asp Val Leu Cys
                660                 665                 670

Trp Leu His Pro Ser Asp Arg Asn Ala Ser Pro Val Lys Arg Asp Val
        675                 680                 685

Ala Phe Gly Glu Phe Tyr Ser Lys Arg Gln Glu Pro Glu Pro Leu Val
        690                 695                 700

Leu Asp Pro Val Thr Gly Tyr Val Lys Ser Thr Leu His Val His Val
705                 710                 715                 720

Cys Arg Asn Gly Glu Asn Gly Ser Thr Ser Gly Thr Pro His His Ala
                725                 730                 735

Gln Glu Ser Met Gln Leu Gly Asn Gly Asp Phe Gly Met Ala Asp Phe
            740                 745                 750

Asp Thr Ile Thr Asn Phe Glu Asn Phe
        755                 760
```

CRYSTAL OF THE N-TERMINAL DOMAIN OF A STAT PROTEIN AND METHODS OF USE THEREOF

GOVERNMENTAL SUPPORT

The research leading to the present invention was supported, at least in part, by NIH Grant Nos. AI32489 and AI34420. Accordingly, the Government may have certain rights in the invention.

FIELD OF THE INVENTION

The present invention relates generally to structural studies of STAT proteins, modified STAT proteins and more particularly the N-terminal domain of STAT proteins. Included in the present invention is a crystal of the N-terminal domain of a STAT protein and corresponding structural information obtained by X-ray crystallography. The present invention also relates to methods of using the crystal and related structural information in drug screening assays.

BACKGROUND OF THE INVENTION

Transcription factors play a major role in cellular function by inducing the transcription of specific mRNAs. Transcription factors, in turn, are controlled by distinct signaling molecules. The STATs (Signal Transducer and Activator of Transcription) constitute a family of transcription factors necessary to activate distinct sets of target genes in response to cytokines and growth factors [Darnell et al. WO 95/08629, (1995)]. The STAT proteins are activated in the cytoplasm by phosphorylation on a single tyrosine residue [Darnell et al., Science 264:1415 (1994)]. The responsible kinases are either ligand-activated transmembrane receptors with intrinsic tyrosine kinase activity, such as EGF- or PDGF-receptors, or cytokine receptors that lack intrinsic kinase activity but have associated JAK kinases, such as those for interferons and interleukins [Ihle, Nature 377:591–594 (1995)]. One distinctive characteristic of the STAT proteins are their apparent lack of requirement for changes in second messenger, e.g., cAMP or $Ca^{++}$, concentrations. Presently, there are seven known mammalian STAT family members. The recent discovery of a Drosophila STAT protein, suggests that these proteins have played an important role in signal transduction since the early stages of our evolution [Darnell, PNAS, 94:11767–11769 (1997)]. Each STAT protein contains a SRC homology domain (SH2 domain). When activated, the STAT proteins are phosphorylated, and form homo- or heterodimeric structures in which the phosphotyrosine of one partner binds to the SH2 domain of the other. The reciprocal SH2-phosphotyrosine interactions between two STAT proteins result in the formation of an active dimer that translocates to the nucleus and activates specific gene expression [Darnell et al., Science 264:1415 (1994)] by binding to a canonical recognition site for the STAT dimer. This canonical recognition site encompasses 9–10 base pairs ($TTCN_{3-4}GAA$) of DNA [Horvath et al., Genes & Devel. 9:984 (1995); Seidel et al., Proc. Natl. Acad. Sci. USA 92:3041 (1995); Ihle, Cell 84:331 (1996); Mikita et al., Mol. Cell. Biol. 16:5811 (1996)]. Analysis of the binding of activated STATs to DNA targets has revealed that the STAT binding sites can extend over two or more adjacent canonical sites [Xu et al., Science 273:750 (1996); Meier and Groner, Mol. Cell. Biol. 14:128 (1994); Symes et al., Molecular Endocrinology 8;1750 (1994); Dajee et al., Molecular Endocrinology 10:171 (1996); John et al., EMBO J. 15:5627 (1996)].

STAT proteins serve in the capacity as a direct messengers between the cytokine or growth factor receptor present on the cell surface, and the cell nucleus. However, since each cytokine and growth factor produce a specific cellular effect by activating a distinct set of genes, the means in which such a limited number of STAT proteins mediate this result remains a mystery. Indeed, at least twenty-five different ligand-receptor complexes signal the nucleus through the seven known mammalian STAT proteins [Yan et al., Cell 84:421–430 (1996)].

There is increasing evidence that mammalian transcription factors activate transcription and achieve biological specificity by interactions with other transcription factors, trans-activators or the general transcription machinery [McKnight, Genes & Development 10:367 (1996); Roeder, Trends in Biochemical Sciences 21:327 (1996)]. Although the molecular basis for these phenomena is poorly understood, direct protein:protein interactions among multiple promoter bound proteins appear to mediate this synergistic activation [Tijan and T. Maniatis, Cell 77:5 (1994)].

In the case of the STATs, a small N-terminal domain has been shown to mediate a number of important protein:protein interactions that influence transcriptional outcome [Leung et al., Science 273:750 (1996); Vinkemeier et al., EMBO J. 15: 5616 (1996)]. This domain allows cooperative interactions between STAT dimers bound to adjacent target sites on DNA, leading to a drastically prolonged half-life of the protein-DNA complex [Vinkemeler et al., EMBO J. 15: 5616 (1996)]. Functional assays exploring the induction of the hepatic Spi 2.1 gene revealed the necessity for cooperative STAT binding to two adjacent recognition sites for a full growth hormone response [Bergad et al., J. Biol. Chem. 270, 24903 (1995)]. In addition, it was observed that these cooperative contacts affect the binding site selection of different STATs on a natural promoter that contains multiple potential STAT recognition sites [Xu et al., Science 273:750 (1996)]. Each of the oligomerized STAT-1, -4, and -5 dimers were shown to bind to a different combination of canonical sites [Xu et al., Science 273:750 (1996)]. Deletion of the N-terminal ~100 residues of STAT-1 and STAT-4 abolishes cooperative binding to DNA [Xu et al., Science 273:750 (1996); Vinkemeier et al., EMBO J. 15: 5616 (1996)]. The truncated protein fully retains binding to a single target site as a dimer, suggesting that the N-terminal domain is dispensable for dimer formation and DNA binding [Xu et al., Science 273:750 (1996); Vinkemeier et al., EMBO J. 15: 5616 (1996)], but is necessary for interaction between STAT dimers and binding site discrimination [Xu et al., Science 273:750 (1996)]. Also, the N-domain of STAT-1 is required for interaction between STAT-1 and the transcriptional co-activator protein CBP, a large (~2500 amino acids) polypeptide with transacetylase activity [Zhang et al., Proc. Natl. Acad. Sci. USA 93:15092 (1996)]. Additionally, the amino-terminal region of STAT-2 is involved in binding to the intracellular region of the interferon-α receptor [Leung et al., Mol. Cell. Biol. 15:1312 (1995)].

Therefore, there is a need to obtain agonists and antagonists that can modulate the effect of STAT proteins during specific gene activation. In particular, there is a need to obtain drugs that will directly interact with the important N-terminal domain of STAT proteins. Unfortunately, identification of such drugs have heretofore relied on serendipity and/or systematic screening of large numbers of natural and synthetic compounds. A far superior method of drug-screening relies on structure based drug design. In this case, the three dimensional structure of a protein or protein fragment is determined and potential agonists and/or potential antagonists are designed with the aid of computer modeling [Bugg et al., *Scientific American*, December:92–98 (1993); West et al., *TIPS*, 16:67–74 (1995)]. However, heretofore the three-dimensional structure of a STAT protein or fragment thereof has remained unknown, essentially because no such protein crystals had been produced of sufficient quality to allow the required X-ray crystallographic data to be obtained.

Therefore, there is presently a need for obtaining an N-terminal STAT domain fragment that can be crystallized to form a crystal with sufficient quality to allow such crystallographic data to be obtained. Further, there is a need for such crystals. Furthermore there is a need for the determination of the three-dimensional structure of such crystals. Finally, there is a need for procedures for related structural based drug design based on such crystallographic data.

The citation of any reference herein should not be construed as an admission that such reference is available as "Prior Art" to the instant application.

SUMMARY OF THE INVENTION

The present invention provides a crystal containing the N-terminal domain of a STAT protein which effectively diffracts X-rays and thereby allows the determination of the atomic coordinates of the N-terminal domain to a resolution of greater than 5.0 Angstroms. In a preferred embodiment of this type the crystal effectively diffracts X-rays for the determination of the atomic coordinates of the N-terminus to a resolution of greater than 3.0 Angstroms. In a more preferred embodiment of this type the crystal effectively diffracts X-rays for the determination of the atomic coordinates of the N-terminus to a resolution of greater than 2.0 Angstroms.

In one embodiment the N-terminal domain of the crystal comprises the amino acid sequence of:

Arg Xaa $^H$Xaa Leu Xaa Xaa Trp $^H$Xaa Glu Xaa Gln Xaa Trp (SEQ ID NO:1), where $^H$Xaa can be either Ile, Leu, Val, Phe, or Tyr and Xaa can be any amino acid. In another embodiment the crystal of the N-terminal domain of the STAT protein is contained in a STAT fragment that consists of 100 to 150 amino acids. In a preferred embodiment the STAT fragment comprises amino acids 4–112 of SEQ ID NO:9. In a more preferred embodiment the crystal contains an N-terminal domain of a STAT protein comprising amino acid residues 2–123 of SEQ ID NO:9 with 5 additional amino acid residues N-terminal to amino acid residue number 2, i.e., from the N-terminus GLY SER GLY GLY GLY (SEQ ID NO:3), amino acid residue 2. In one embodiment of this type the crystal effectively diffracts X-rays to allow the determination of the atomic coordinates of the N-terminus to a resolution of 1.45 Angstroms.

The present invention provides a crystal of the N-terminal domain having a space group of P6$_5$22 and a unit cell of dimensions a=79.51 Å, b=79.51 Å, and c=84.68 Å. The present invention further provides a crystal of the N-terminal domain having secondary structural elements comprising eight helices (α1–α8) that are assembled into a hook-like structure that has an inner and outer surface. The first four helices (α1–α4) form a ring-shaped element having a proximal and a distal surface, whereas helices six (α6) and seven (α7) form an anti-parallel coiled-coil that also has a proximal and a distal surface. Helix five (α5) connects the ring-shaped element to the anti-parallel coiled-coil, while helix eight (α8) is wrapped around the distal surface of the ring-shaped element. The inner surface of the hook-like structure is formed by the intersection of the proximal surface of the ring-shaped element with the proximal surface of the antiparallel coiled-coil.

The present invention also provides a method of growing a crystal of an N-terminal domain of a STAT protein. The method of making the crystal comprises placing an aliquot of a solution containing a STAT N-terminal domain fragment of the present invention on a cover slip as a hanging drop above a well containing a reservoir buffer that comprises 0.2 M Na$^+$CH$_3$COO$^-$, 0.1 M Tris/HCL pH 8.0, 17% PEG4000. All of the STAT N-terminal domain fragments of the present invention may be used in this manner to prepare such a crystal. In one specific embodiment the solution containing a STAT N-terminal domain fragment is prepared by combining a preparation of the STAT N-terminal domain fragment that contains 20 mg/ml of the STAT N-terminal domain fragment in 50 mM Hepes/HCl pH 8.0, 150 mM KCl, 2.5 mM CaCl$_2$, and 5 mM DTT with an equal volume of the reservoir buffer. In a preferred embodiment the aliquot comprises approximately 1 μl of the solution. In another preferred embodiment the STAT N-terminal domain fragment comprises the amino acid sequence of:

Arg Xaa $^H$Xaa Leu Xaa Xaa Trp $^H$Xaa Glu Xaa Gln Xaa Trp (SEQ ID NO:1), where $^H$Xaa can be either Ile, Leu, Val, Phe, or Tyr. In a more preferred embodiment the N-terminal domain is a STAT-4 N-terminal domain fragment. In a still more preferred embodiment the STAT-4 N-terminal domain fragment contains amino acid residues 2–123 of SEQ ID NO:9 with 5 additional amino acid residues N-terminal to amino acid residue number 2, i.e., from the N-terminus GLY SER GLY GLY GLY (SEQ ID NO:3), amino acid residue 2.

The present invention also provides methods of screening drugs that either enhance or inhibit STAT-STAT dimeric interactions. Such methods include those that identify drugs that effect the interaction of N-terminal domains of STAT proteins that are bound to adjacent DNA binding sites. In one such embodiment, a drug library is screened by assaying the binding activity of a STAT protein to its DNA binding site. This assay is based on the ability of the N-terminal domain of STAT proteins to substantially enhance the binding affinity of two adjacent STAT dimers to a pair of closely aligned DNA binding sites, i.e., binding sites separated by approximately 10 to 15 base pairs. Such drug libraries include phage libraries as described below, chemical libraries compiled by the major drug manufacturers, mixed libraries, and the like. Any of such compounds contained in the drug libraries are suitable for testing as a prospective drug in the assays described below, including in a high throughput assay based on the methods described below.

An antagonist of the STAT N-terminal dimeric interaction antagonizes one or more aspects of the binding of the STAT dimers to adjacent weak binding sites for the STAT dimers on a promoter of a gene. Such antagonists could be useful as drugs in the treatment of a variety of disease states, including inflammation, allergy, asthma, and leukemias.

On the other hand, a drug that acts as an agonist stabilizes the N-terminal dimeric interaction between STAT dimers bound to adjacent weak binding sites for the STAT dimers on a promoter of a gene, thereby enhancing STAT function. Such agonists can be used as drugs that are useful in the treatment of anemias, neutropenias, thrombocytopenia, cancer, obesity, viral diseases and growth retardation, or other diseases characterized by an insufficient STAT activity.

Therefore the present invention provides a method of using the crystals of the present invention in drug screening assays. In one such embodiment the method comprises selecting a potential drug by performing rational drug design with the three-dimensional structure determined for the crystal. The selecting is preferably performed in conjunction with computer modeling. The potential drug is contacted with a dimeric STAT protein N-terminal domain and the binding of the potential drug with the N-terminal domain is detected. A drug is selected which binds to the N-terminal domain of the dimeric STAT protein.

In a preferred embodiment of this type, contacting the potential drug with a dimeric STAT protein N-terminal domain is performed with dimeric STAT protein fragments containing the STAT protein N-terminal domain. In a more preferred embodiment the STAT protein N-terminal domain has an amino acid sequence comprising SEQ ID NO:1. In one such embodiment the dimeric STAT protein fragment is labeled. In another such embodiment the dimeric STAT protein fragment is bound to a solid support.

Another method of using a crystal of the present invention in a drug screening assay comprises selecting a potential drug by performing rational drug design with the three-dimensional structure determined for the crystal. The selecting is preferably performed in conjunction with computer modeling. The potential drug is contacted with two or more dimeric STAT proteins in the presence of a nucleic acid containing at least two adjacent weak binding sites for STAT protein dimers and the effect of the potential drug on the binding of the dimeric STAT proteins to each other and/or to the nucleic acid is detected. A potential drug is selected as a candidate drug when it either enhances or diminishes the binding of the dimeric STAT proteins to each other and/or the nucleic acid. In a preferred embodiment of this type the method further comprises growing a supplemental crystal containing a protein-drug complex formed between the dimeric N-terminal domain of the STAT protein and the candidate drug. A crystal is chosen that effectively diffracts X-rays allowing the determination of the atomic coordinates of the protein-ligand complex to a resolution of greater than 5.0 Angstroms, preferably to a resolution greater than 3.0 Angstroms and more preferably to a resolution greater than 2.0 Angstroms. The three-dimensional structure of the supplemental crystal is determined by molecular replacement analysis and a drug is selected by performing rational drug design with the three-dimensional structure determined for the supplemental crystal. The selecting is preferably performed in conjunction with computer modeling.

The present invention also provides a method for identifying a drug that modulates the ability of adjacent STAT protein dimers to interact and bind to adjacent DNA binding sites. One such embodiment comprises selecting a potential drug by performing rational drug design with the three-dimensional structure determined for a crystal of the present invention. The selecting is preferably performed in conjunction with computer modeling. The binding affinity of the STAT protein (or of a fragment thereof that comprises the N-terminal domain) for a nucleic acid comprising two adjacent weak STAT DNA binding sites in the presence and absence of the potential drug is determined (i.e., measured). The binding affinity of the STAT protein (or the fragment) for a nucleic acid comprising a single strong STAT binding site in the presence and absence of the potential drug is also determined. Next a comparison is made between the binding affinities of the STAT protein (or the fragment) is measured for the two adjacent weak STAT DNA binding sites in the presence and absence of the potential drug with that determined for the STAT protein (or the fragment) for the single strong STAT binding site in the presence and absence of the potential drug. A potential drug which causes an increase in the binding affinity measured for the two adjacent weak STAT DNA binding sites but not in the binding affinity measured for the single strong STAT binding site is identified as a drug that enhances the interaction between adjacent activated STAT dimers. On the other hand, a potential drug which causes a decrease in the binding affinity measured for the two adjacent weak STAT DNA binding sites but not in the binding affinity measured for the single strong STAT binding site is identified as a drug that inhibits the interaction between adjacent activated STAT dimers.

The present invention further provides a method for identifying a drug that modulates the ability of adjacent STAT protein dimers to interact and bind to adjacent DNA binding sites which comprises measuring the binding affinity of the STAT protein comprising a functional N-terminal domain to a nucleic acid comprising two adjacent weak STAT DNA binding sites in the presence and absence of a potential drug. The binding affinity of a modified form of the STAT protein that lacks a functional N-terminal domain is also determined for the nucleic acid in the presence and absence of the potential drug. The binding affinity measured for the STAT protein in the presence and absence of the potential drug is then compared with the binding affinity measured for the modified STAT protein in the presence and absence of the potential drug. A potential drug which causes an increase in the binding affinity measured for the functional STAT protein but not in the binding affinity measured for the modified STAT protein is identified as a drug that enhances the interaction between adjacent activated STAT dimers, and a potential drug which causes a decrease in the binding affinity measured for the STAT protein but not in the binding affinity measured for the modified STAT protein is identified as a drug that inhibits the interaction between adjacent activated STAT dimers. Variations of these assays are performed in in situ assays as described below with reporter genes operably under the control of weak and/or strong STAT binding sites.

In one such embodiment the modified STAT protein is a STAT protein that lacks the α4-tryptophan. In another such embodiment the modified Stat protein lacks the α4-glutamic acid. In still another embodiment the modified STAT protein is the truncated STAT protein Stat1tc identified in by Vinkemeier et al.[*EMBO J.* 15:5616 (1996)].

The present invention further provides a method for identifying a drug that enhances or diminishes the ability of STAT protein dimers to induce the expression of a gene operably under the control of a promoter containing at least two adjacent weak binding sites for STAT protein dimers. One such embodiment comprises selecting a potential drug by performing rational drug design with the three-dimensional structure determined for a crystal of the present invention. The selecting is preferably performed in conjunction with computer modeling. The level of expression of a first reporter gene and a second reporter gene contained by a host cell in the presence and absence of the potential drug is determined. The first reporter gene is operably linked to a first promoter containing at least two adjacent weak binding sites for STAT protein dimers, and the second reporter gene is operably linked to a second promoter comprising at least one strong binding site for a STAT protein dimer. The binding of STAT protein dimers to the two adjacent weak binding sites induces the expression of the first reporter gene, and the binding of the STAT protein dimer to the strong binding site induces the expression of the second reporter gene. In addition the host cell either naturally contains STAT protein dimers or is modified and/or induced to contain them. The level of expression of the first reporter gene is then compared with that of the second reporter gene in the presence and absence of the potential drug. When the presence of the potential drug results in an increase in the level of expression of the first reporter gene but not that of the second reporter gene, the potential drug is identified as a drug that enhances the ability of STAT protein dimers to induce the expression of a gene operably under the control of a promoter containing at least two adjacent weak binding sites for STAT protein dimers. On the other hand, when the presence of a potential drug results in a decrease in the level of expression of the first reporter gene but not that of the second reporter gene, the potential drug is identified as a drug that inhibits the ability of STAT protein dimers to induce the expression of a gene operably under the control of a promoter containing at least two adjacent weak binding sites for STAT protein dimers.

In a preferred embodiment of this type, the method further comprises growing a supplemental crystal containing a protein-drug complex formed between the dimeric N-terminal domain and the drug. The crystal effectively diffracts X-rays allowing the determination of the atomic coordinates of the protein-ligand complex to a resolution of greater than 5.0 Angstroms, preferably to a resolution of greater than 3.0 Angstroms and more preferably to a resolution of greater than 2.0 Angstroms. The three-dimensional structure of the supplemental crystal is then determined with molecular replacement analysis.

A drug is selected by performing rational drug design with the three-dimensional structure determined for the supplemental crystal. The selecting is preferably performed in conjunction with computer modeling.

In an alternative embodiment, the first reporter gene is contained by a first host cell, and the second reporter gene is contained by a second host cell. In this case, both the first host cell and second host cell contain STAT protein dimers. In one embodiment, the weak STAT binding sites are from sites present in the regulatory regions of the MIG gene. In another embodiment the weak STAT binding sites are from sites present in the regulatory regions of the c-fos gene. In still another embodiment the weak STAT binding sites are from sites present in the regulatory regions of the interferon-γ gene. In a related embodiment the mutated cfos-promotor element, the M67 site [Wagner et al., *EMBO J.* 9:4477 (1990)] is used as the strong STAT binding site. In another embodiment of this type the strong STAT binding site is the S1 site [Horvath et al., *Genes & Devel.* 9:984 (1995)]. In still another such embodiment strong STAT binding site is obtained from the IRF-1 gene promoter. In preferred embodiments, the host cell or host cells are mammalian cells.

These and other aspects of the present invention will be better appreciated by reference to the following drawings and Detailed Description.

BRIEF DESCRIPTION OF THE DRAWINGS

FIG. 2: Tertiary structure of the amino-terminal domain of STAT-4. FIG. 2A depicts the overall representation of two monomers (green and gray) in the crystallographic dimer, viewed approximately orthogonal to the molecular 2-fold axis, which is vertical. The ring-shaped N-terminal element is colored red in one monomer. FIG. 2B depicts the orthogonal view of one of the N-terminal domains shown in FIG. 2A, showing details of the architecture of the ring-shaped element. Side chains that participate in a charge stabilized hydrogen-bond network are shown in a ball-and-stick representation. The side chain and backbone carbonyl of buried Arg 31 are shown in magenta. For clarity, the indole ring of the invariant residue Trp 4 that seals off this arrangement on the proximal side is drawn with thinner bonds. The blue sphere denotes a buried water molecule. Hydrogen-bonds are indicated by dotted lines. Oxygen, nitrogen, and carbon atoms are colored red, blue and yellow, respectively. Q3-N marks the position of the backbone amide group of residue Gln 3. The light red colored segment of helix α2 highlights its $3_{10}$ helical conformation. FIGS. 2, 3B, and 3C were created with the program RIBBONS v2.0 [Carson, *J. Appl. Cryst.* 24:958 (1991)].

FIG. 3B shows a view at the dimerization interface with amino acids represented as ball-and-stick models and the cα backbone as ribbon. The monomer is in the same orientation as the one on the right of panel of FIG. 3A. Side chains are colored according to their position following the same convention as in FIG. 3A; backbone ribbon is colored as in FIG. 2B with the first 40 residues highlighted in red. Note the entirely polar nature of the interface. Leu 33 makes a backbone carbonyl group contact and its position is represented by the filled circle. In the STAT-4 recombinant N-terminal domain used for crystallization, Met 1 was replaced with Gly plus four additional small amino acids, one of which (Gly-1) is visible in the electron density map (see Methods in the EXAMPLE below). In the crystals the amino terminus of Gly-1 is part of the dimer interface, possibly substituting for the native Met 1. FIG. 3C shows the close-up stereo view of intermolecular hydrogen bonding network in the dimer. Selected side chains surrounding the conserved Trp 37 (magenta) in helices α4 and α6 of two monomers (green and grey) are shown. Trp 37 makes direct (E 66') and water mediated contacts (Q 63'). Water molecules are depicted as blue spheres.

FIG. 4 indicates the importance of the invariant residue Trp 37 for STAT-1 tetramerization and mediation of gene activation.

DETAILED DESCRIPTION OF THE INVENTION

The present invention provides the first three-dimensional structural information regarding the important family of transcription factors known as STATS. More particularly, the present invention provides a crystalline form of the N-terminal cooperative domain (more simply denoted as the N-terminal domain) of a STAT protein of sufficient quality to perform meaningful X-ray crystallographic measurements. In addition, the present invention provides a method of preparing such crystals.

In addition the present invention provides a method of using the crystals and the crystallographic measurements for drug discovery and development. These methods include procedures for screening drugs that either enhance or inhibit STAT-STAT dimer interactions, which can have a critical effect on the transcription of the specific genes under the control of STAT proteins. For example, antagonists of the STAT N-terminal dimer interaction antagonize STAT functions dependent on this aspect of STAT behavior. Drugs that are antagonists would be useful for the treatment of a variety of disease states, including but not limited to, inflammation, allergy, asthma, and leukemias. On the other hand, drugs that are found to be agonists would stabilize the N-terminal interaction between STAT dimers, thereby enhancing this aspect of the STAT function. Such drugs may therefore have utility in the treatment of anemias, neutropenias, thrombocytopenia, cancer, obesity, viral diseases and growth retardation, or other diseases characterized by a insufficient STAT activity.

Therefore, if appearing herein, the following terms shall have the definitions set out below.

Figure 1A:
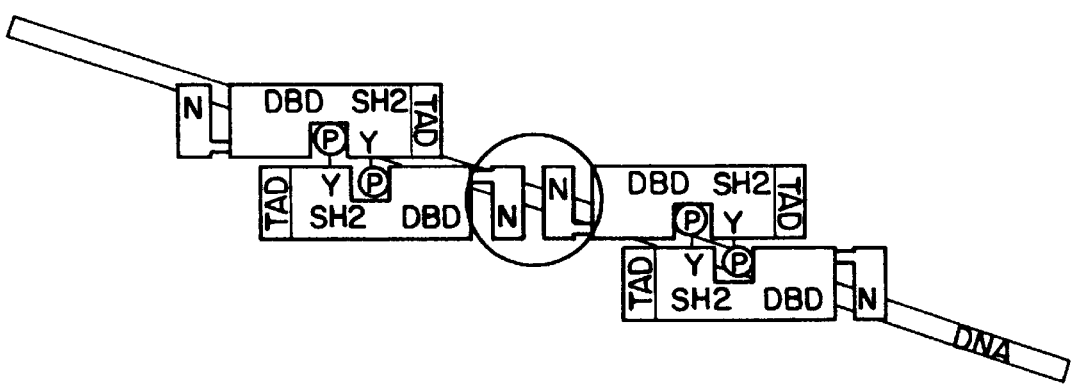
FIG. 1A shows a schematic representation of two STAT dimers bound to adjacent target sites. Interactions between N-domains (N, circled) allow the dimers to bind to each other. Phosphotyrosines are indicated as "Y" with encircled P symbols. DBD: DNA binding domain; SH2: SH2 domain; TAD: transactivation domain.

As used herein the "α4-tryptophan" is the conserved tryptophan common in all STAT proteins found in the N-terminal domain in an alpha helix defined as α4 in FIG. 1. For mStat4 the α4-tryptophan is $W_{37}$ of the amino acid sequence. Similarly, the α4-glutamic acid is the conserved glutamic acid common in all STAT proteins found in the N-terminal domain in an alpha helix defined as α4 in FIG. 1. For mStat4 the α4 glutamic acid is $E_{39}$ of the amino acid sequence.

As used herein a the term "STAT protein" includes a particular family of transcription factor consisting of the Signal Transducers and Activators of Transcription proteins. These proteins have been defined in International Patent Publication No.s WO 93/19179 (Sep. 30, 1993, by James E. Darnell, Jr. et al.), WO 95/08629 (Mar. 30, 1995, by James E. Darnell, Jr. et al.) and United States application having a Ser. No. 08/212,184, filed on Mar. 11, 1994, entitled, "Interferon Associated Receptor Recognition Factors, Nucleic Acids Encoding the Same and Methods of Use Thereof" by James E. Darnell, Jr. et al., all of which are incorporated by reference in their entireties, herein. Currently, there are seven STAT family members which have been identified, numbered STAT 1, 2, 3, 4, 5A, 5B, and 6. STAT proteins include proteins derived from alternative splice sites such as Human STAT1α and STAT1β, i.e., STAT1β is a shorter protein than STAT1α and is translated from an alternatively spliced mRNA. Modified STAT proteins and functional fragments of STAT proteins are included in the present invention.

As used herein the terms "phosphorylated" and "nonphosphorylated" as used in conjunction with or in reference to a STAT protein denote the phosphorylation state of a particular tyrosine residue of the STAT proteins (e.g., Tyr 701 of STAT1). When STAT proteins are phosphorylated, they form homo- or heterodimeric structures in which the phosphotyrosine of one partner binds to the SRC homology domain (SH2) of the other. In their natural environment the newly formed dimer then translocates from the cytoplasm to the nucleus, binds to a palindromic GAS sequence, thereby activating transcription.

The "N-terminal domain" of a STAT protein is used interchangeably herein with the "N-terminal cooperative domain" and refers to the N-terminal portion of a STAT protein involved in STAT protein dimer-dimer interaction at a weak STAT DNA binding site. Preferably the amino acid of the N-terminal domain comprises SEQ ID NO:1. In one particular embodiment the STAT protein is STAT-4 comprising amino acids 2–123 of SEQ ID NO:9.

General Techniques for Constructing Nucleic Acids that Express Recombinant STAT Proteins In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences and synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "homologous" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins have sequence homology as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding a STAT protein, whether genomic DNA or cDNA, can be isolated from any animal source, particularly from a mammal. Methods for obtaining the STAT protein gene are well known in the art, as described above (see, e.g., Sambrook et al., 1989, supra).

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

The present invention also relates to cloning vectors containing genes encoding analogs and derivatives of the STAT protein, including modified STAT proteins of the invention, that have the same or homologous functional activity as STAT protein, and homologs thereof.

The production and use of derivatives and analogs related to the STAT protein are within the scope of the present invention.

STAT protein derivatives and analogs as described above can be made by altering encoding nucleic acid sequences by substitutions, e.g. replacing the α4-tryptophan or α4-glutamic acid with an alanine, or additions or deletions that provide for functionally equivalent or specifically modified molecules.

Due to the degeneracy of nucleotide coding sequences, other DNA sequences which encode substantially the same amino acid sequence as a nucleic acid encoding a modified STAT protein or an N-terminal STAT protein fragment of the present invention (including the fragment which lacks the α4-tryptophan) may be used in the practice of the present invention. These include but are not limited to allelic genes, homologous genes from other species, which are altered by the substitution of different codons that encode the same amino acid residue within the sequence, thus producing a silent change. Likewise, the modified STAT protein derivatives of the invention include, but are not limited to, those containing, as a primary amino acid sequence, all or part of the amino acid sequence of a STAT protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Particularly preferred conserved amino acid exchanges are:

(a) Lys for His or for Arg or vice versa such that a positive charge may be maintained;
(b) Glu for Asp or vice versa such that a negative charge may be maintained;
(c) Ser for Thr or vice versa such that a free —OH can be maintained;
(d) Gln for Asn or vice versa such that a free $NH_2$ can be maintained;
(e) Ile for Leu or for Val or vice versa as roughly equivalent hydrophobic amino acids; and
(f) Phe for Tyr or vice versa as roughly equivalent aromatic amino acids.

Non-conserved amino acid substitutions may also be introduced to substitute an amino acid with a particularly preferable property. For example, a Cys may be introduced to provide a potential site for disulfide bridges with another Cys. A His may be introduced as a particular "catalytic" site (i.e., His can act as an acid or base and is the most common amino acid in biochemical catalysis). Pro may be introduced because of its particularly planar structure, which induces β-turns in the protein's structure.

The genes encoding STAT proteins, and derivatives and analogs thereof can be produced by various methods known in the art. The manipulations which result in their production can occur at the gene or protein level. For example, the cloned N-terminal domain of a STAT protein gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of a STAT protein care should be taken to ensure that the modified gene remains within the same translational reading frame as the STAT protein gene, uninterrupted by translational stop signals, in the gene region where the desired activity is encoded.

Additionally, the STAT protein-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast $2\mu$ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of STAT Proteins

The nucleotide sequence coding for a STAT protein, or functional fragment, including the N-terminal peptide fragment of a STAT protein, derivatives or analogs thereof, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a STAT protein of the invention or functional fragment, including the N-terminal peptide fragment of a STAT protein, derivatives or analogs thereof, is operationally associated with a promoter in an expression vector of the invention. Both cDNA and genomic sequences can be cloned and expressed under control of such regulatory sequences. An expression vector also preferably includes a replication origin. The necessary transcriptional and translational signals can be provided on a recombinant expression vector. As detailed below, all genetic manipulations described for the STAT gene in this section, may also be employed for genes encoding a functional fragment, including the N-terminal domain peptide fragment of a STAT protein, derivatives or analogs thereof, including a chimeric protein, thereof.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant STAT protein of the invention, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding STAT protein is cultured in an appropriate cell culture medium under conditions that provide for expression of STAT protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of STAT protein may be controlled by any promoter/enhancer element known in the art, but these regulatory elements must be functional in the host selected for expression.

Expression vectors containing a nucleic acid encoding a STAT protein of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding STAT protein is inserted within the "selection marker" gene sequence of the vector, recombinants containing the STAT protein insert can be identified by the absence of the STAT protein gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, nonchromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglIII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedron initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XhaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Yeast expression systems can also be used according to the invention to express OB polypeptide. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the present invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Synthetic Polypeptides

The term "polypeptide" is used in its broadest sense to refer to a compound of two or more subunit amino acids, amino acid analogs, or peptidomimetics. The subunits are linked by peptide bonds. The STAT proteins and more particularly the N-terminal domain fragments thereof, of the present invention may be chemically synthesized.

More particularly, potential drugs that may be tested in the drug screening assays of the present invention may also be chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile $N^\alpha$-amino protected 9-fluorenylmethoxycarbonyl (Fmoc) amino acids first described by Carpino and Han (1972, J. Org. Chem. 37:3403–3409). Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other N$^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189–199; Hruby et al., 1990, Biochem J. 268:249–262); the present invention provides a method to produce a constrained peptide that incorporates random sequences at all other positions.

Constrained and cyclic peptides. A constrained, cyclic or rigidized peptide may be prepared synthetically, provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson (1980, Biophys. Biochem. Res. Commun. 94:1128–1132). A peptide in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The present invention provides strategies to systematically prepare cross-links. For example, if four cysteine residues are incorporated in the peptide sequence, different protecting groups may be used (Hiskey, 1981, in The Peptides: Analysis, Synthesis, Biology, Vol. 3, Gross and Meienhofer, eds., Academic Press: New York, pp. 137–167; Ponsanti et al., 1990, Tetrahedron 46:8255–8266). The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids that induce conformational constraints. The following non-classical amino acids may be incorporated in the peptide in order to introduce particular conformational motifs: 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); -helix inducing analogs (Kemp et al., 1988, Tetrahedron Lett. 29:4935–4938); γ-turn inducing analogs (Kemp et al., 1989, J. Org. Chem. 54:109:115); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110:5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

Crystals of the N-Terminal Domain Fragment of a STAT Protein

Crystals of the N-terminal domain fragment of a STAT protein can be grown by a number of techniques including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used.

As exemplified below hanging drops of one μl of the STAT-4 N-terminal domain fragment (20 mg/ml, in 50 mM Hepes/HCl pH 8.0, 150 mM KCl, 2.5 mM $CaCl_2$, 5 mM DTT) was mixed with equal volumes of reservoir buffer containing 0.2 M $Na^+CH_3COO^-$, 0.1 M Tris/HCL pH 8.0, 17% PEG4000. Hexagonal crystals (0.2×0.2×0.2 mm) were routinely grown overnight at 20° C.

Once a crystal of the present invention is grown, X-ray diffraction data can be collected. The Example below used a MAR imaging plate detector for X-ray diffraction data collection though alternative methods may also be used. For example, crystals can be characterized by using X-rays produced in a conventional source (such as a sealed tube or a rotating anode) or using a synchrotron source. Methods of characterization include, but are not limited to, precision photography, oscillation photography and diffractometer data collection. Heavy atom derivatives such as produced with a mercurial, exemplified below, can be performed using Fuji imaging plates. Alternatively, the STAT fragment can be synthesized with selenium-methionine (Se-Met) in place of methionine, and the Se-Met multiwavelength anomalous dispersion data [Hendrickson, Science, 254:51–58 (1991)] can be collected on CHESS F2, using reverse-beam geometry to record Friedel pairs at four X-ray wavelengths, corresponding to two remote points above and below the Se absorption edge ($\lambda_1$ and $\lambda_4$) and the absorption edge inflection point ($\lambda_2$) and peak ($\lambda_3$). Selenium sites can be located using SHELXS-90 in Patterson search mode (G. M. Sheldrick). Experimental phases ($\alpha_{MAD}$) can be estimated via a multiple isomorphous replacement/anomalous scattering strategy using MLPHARE (Z. Otwinowski, Southwestern University of Texas, Dallas) with three of the wavelengths treated as derivatives and one ($\lambda_2$) treated as the parent for example. In either case, data can be processed using HKL, DENZO and SCALEPACK (Z. Otwinowski and W. Minor).

In addition, X-PLOR, as used in the Example below [Brüger, X-PLOR v. 3.1 Manual, New Haven: Yale University, (1993B)] or Heavy [T. Terwilliger, Los Alamos National Laboratory] may be utilized for bulk solvent correction and B-factor scaling. After density modification and non-crystallographic averaging, the protein is built into a electron density map using the program O, as exemplified below [Jones et al., Acta Cryst., A47:110–119 (1991)]. Model building interspersed with positional and simulated annealing refinement [Brünger, 1993B, supra] can permit the an unambiguous trace and sequence assignment of the N-terminal domain fragment of the STAT protein.

Protein-Structure Based Design of Agonists and Antagonists of STAT Proteins

Once the three-dimensional structure of a crystal comprising a an N-terminal domain fragment of a STAT protein is determined, a potential ligand (antagonist or agonist) is examined through the use of computer modeling using a docking program such as GRAM, DOCK, or AUTODOCK [Dunbrack et al., 1997, supra]. This procedure can include computer fitting of potential ligands to the STAT dimer to ascertain how well the shape and the chemical structure of the potential ligand will complement or interfere with the dimer-dimer interaction. [Bugg et al., Scientific American, December:92–98 (1993); West et al., TIPS, 16:67–74 (1995)]. Computer programs can also be employed to estimate the attraction, repulsion, and steric hindrance of the ligand to the dimer-dimer binding site. Generally the tighter the fit (e.g., the lower the steric hindrance, and/or the greater the attractive force) the more potent the potential drug will be since these properties are consistent with a tighter binding constant. Furthermore, the more specificity in the design of a potential drug the more likely that the drug will not interfer with other properties of the STAT protein or other proteins (particularly proteins present in the nucleus). This will minimize potential side-effects due to unwanted interactions with other proteins.

Initially a potential ligand could be obtained by screening a random peptide library produced by recombinant bacteriophage for example, [Scott and Smith, Science, 249:386–390 (1990); Cwirla et al., Proc. Natl. Acad. Sci., 87:6378–6382 (1990); Devlin et al., Science, 249:404–406 (1990)] or a chemical library. A ligand selected in this manner could be then be systematically modified by computer modeling programs until one or more promising potential ligands are identified. Such analysis has been shown to be effective in the development of HIV protease inhibitors [Lam et al., Science 263:380–384 (1994); Wlodawer et al., Ann. Rev. Biochem. 62:543–585 (1993); Appelt, Perspectives in Drug Discovery and Design 1:23–48 (1993); Erickson, Perspectives in Drug Discovery and Design 1:109–128 (1993)].

Such computer modeling allows the selection of a finite number of rational chemical modifications, as opposed to the countless number of essentially random chemical modifications that could be made, and of which any one might lead to a useful drug. Each chemical modification requires additional chemical steps, which while being reasonable for the synthesis of a finite number of compounds, quickly becomes overwhelming if all possible modifications needed to be synthesized. Thus through the use of the three-dimensional structure disclosed herein and computer modeling, a large number of these compounds can be rapidly screened on the computer monitor screen, and a few likely candidates can be determined without the laborious synthesis of untold numbers of compounds.

Once a potential ligand (agonist or antagonist) is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential ligand may be synthesized de novo. As mentioned above, the de novo synthesis of one or even a relatively small group of specific compounds is reasonable in the art of drug design. The prospective drug can be placed into any standard binding assay described below to test its effect on the dimeric N-terminal domain STAT-STAT interaction.

When a suitable drug is identified, a supplemental crystal can be grown which comprises a protein-ligand complex formed between an N-terminal domain of the STAT protein and the drug. Preferably the crystal effectively diffracts X-rays allowing the determination of the atomic coordinates of the protein-ligand complex to a resolution of greater than 5.0 Angstroms, more preferably greater than 3.0 Angstroms, and even more preferably greater than 2.0 Angstroms. The three-dimensional structure of the supplemental crystal can be determined by Molecular Replacement Analysis. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR and AMORE [J. Navaza, Acta Crystallographics ASO, 157–163 (1994)]. Once the position and orientation are known an electron density map can be calculated using the search model to provide X-ray phases. Thereafter, the electron density is inspected for structural differences and the search model is modified to conform to the new structure. Using this approach, it will be possible to use the claimed structure of the N-terminal domain STAT fragment to solve the three-dimensional structures of any such STAT fragment. Other computer programs that can be used to solve the structures of such STAT crystals include QUANTA, CHARMM; INSIGHT; SYBYL; MACROMODE; and ICM.

For all of the drug screening assays described herein further refinements to the structure of the drug will generally be necessary and can be made by the successive iterations of any and/or all of the steps provided by the particular drug screening assay.

Phage libraries for Drug Screening.

Phage libraries have been constructed which when infected into host *E. coli* produce random peptide sequences of approximately 10 to 15 amino acids [Parmley and Smith, Gene 73:305–318 (1988), Scott and Smith, Science 249:386–249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive N-terminal peptide fragment of a STAT protein (e.g., a fragment having an amino acid sequence comprising SEQ ID NO:1). After a specified incubation period, the filters can be thoroughly washed and developed for autoradiography. Plagues containing the phage that bind to the radioactive N-terminal peptide fragment of a STAT protein can then be identified. These phages can be further cloned and then retested for their ability to bind to the N-terminal peptide fragment of a STAT protein as before. Once the phages have been purified, the binding sequence contained within the phage can be determined by standard DNA sequencing techniques. Once the DNA sequence is known, synthetic peptides can be generated which represents these sequences.

These peptides can be tested, for example, for their ability to: (1) interfere with a dimeric STAT protein binding to a weak STAT DNA binding site; and (2) interfere with a dimeric STAT protein lacking the α4-tryptophan and/or a truncated STAT protein in which the N-terminal domain has been removed (e.g., Stat1tc, [Vinkemeier et al., *EMBO J.* 15: 5616 (1996)]) from binding to the same DNA binding site. If the peptide interferes in the first case but does not interfere in the latter case, it may be concluded that the peptide interferes with dimeric N-terminal STAT-STAT interaction.

The effective peptide(s) can be synthesized in large quantities for use in in vivo models and eventually in humans to modulate STAT signal transduction. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, Vaccine 10:175–178 (1990)].

Binding Assays for Drug Screening Assays

The drug screening assays of the present invention may use any of a number of assays for measuring the stability of a STAT-STAT dimeric interaction, including N-terminal dimeric STAT fragments and/or a dimeric STAT-STAT-DNA binding interaction. In one embodiment the stability of a preformed DNA-protein complex between a dimeric STAT protein and its corresponding DNA binding site is examined as follows: the formation of a complex between the STAT protein and a labeled oligonucleotide is allowed to occur and unlabelled oligonucleotides are added in vast molar excess after the reaction reaches equilibrium. At various times after the addition of unlabelled competitor DNA, aliquots are layered on a running native polyacrylamide gel to determine free and bound oligonucleotides. In one preferred embodiment the protein is STAT1α, and two different labeled DNAs are used, the natural cfos site, an example of a "weak" site, and the mutated cfos-promotor element, the M67 site [Wagner et al., *EMBO J.* 9:4477 (1990)] an example of a "strong" site as described below. Other examples of weak sites include those in the promoter of the MIG gene, and those in the regulatory region of the interferon-γ gene. Other examples of strong sites include those such as the selected optimum site, S1 [Horvath et al., *Genes & Devel.* 9:984 (1995)] or the promoter of the IRF-1 gene.

In a related binding assay, a nucleic acid containing a weak STAT binding site is placed on or coated onto a solid support. Methods for placing the nucleic acid on the solid support are well known in the art and include such things as linking biotin to the nucleic acid and linking avidin to the solid support. Dimeric STAT proteins are allowed to equilibrate with the nucleic acid and drugs are tested to see if they disrupt or enhance the binding. Disruption leads to either a faster release of the STAT protein which may be expressed as a faster off time, and or a greater concentration of released STAT dimer. Enhancement leads to either a slower release of the STAT protein which may be expressed as a slower off time, and/or a lower concentration of released STAT protein.

The STAT protein may be labeled as described below. For example, in one embodiment radiolabeled STAT proteins are used to measure the effect of a drug on binding. In another embodiment the natural ultraviolet absorbance of the STAT protein is used. In yet another embodiment, a Biocore chip (Pharmacia) coated with the nucleic acid is used and the change in surface conductivity can be measured.

In yet another embodiment, the affect of a prospective drug (a test compound) on interactions between N-terminal domains of STATs is assayed in living cells that contain or can be induced to contain activated STAT proteins, i.e., STAT protein dimers. Cells containing a reporter gene, such as the heterologous gene for luciferase, green fluorescent protein, chloramphenicol acetyl transferase or β-galactosidase, operably linked to a promoter comprising two weak STAT binding sites are contacted with a prospective drug in the presence of a cytokine which activates the STAT(s) of interest. The amount (and/or activity) of reporter produced in the absence and presence of prospective drug is determined and compared. Prospective drugs which reduce the amount (and/or activity) of reporter produced are candidate antagonists of the N-terminal interaction, whereas prospective drugs which increase the amount (and/or activity) of reporter produced are candidate agonists. Cells containing a reporter gene operably linked to a promoter comprising strong STAT binding sites are then contacted with these candidate drugs, in the presence of a cytokine which activates the STAT(s) of interest. The amount (and/or activity) of reporter produced in the presence and absence of candidate drugs is determined and compared. Drugs which disrupt interactions between dimeric N-terminal domains of the STATs will not reduce reporter activity in this second step. Similarly, candidate drugs which enhance interactions between dimeric N-terminal domains of STATs will not increase reporter activity in this second step.

In an analogous embodiment, two reporter genes each operably under the control of one or the other of the two types promoters described above can be comprised in a single host cell as long as the expression of the two reporter gene products can be distinguished. For example, different modified forms of green fluorescent protein can be used as described in U.S. Pat. No. 5,625,048, Issued Apr. 29, 1997, hereby incorporated by reference in its entirety.

Although cells that naturally encode the STAT proteins may be used, preferably a cell is used that is transfected with a plasmid encoding the STAT protein. For example transient transfections can be performed with 50% confluent U3A cells using the calcium phosphate method as instructed by the manufacturer (Stratagene). In addition as mentioned above, the cells can also be modified to contain one or more reporter genes, a heterologous gene encoding a reporter such as luciferase, green fluorescent protein or derivative thereof, chloramphenicol acetyl transferase, β-galactosidase, etc. Such reporter genes can individually be operably linked to promoters comprising two weak STAT binding sites and/or a promoter comprising a strong STAT binding site. Assays for detecting the reporter gene products are readily available in the literature. For example, luciferase assays can be performed according to the manufacturer's protocol (Promega), and β-galactosidase assays can be performed as described by Ausubel et al., [in Current Protocols in Molecular Biology, J. Wiley & Sons, Inc. (1994)].

In one example, the transfection reaction can comprise the transfection of a cell with a plasmid modified to contain a STAT protein, such as a pcDNA3 plasmid (Invitrogen), a reporter plasmid that contains a first reporter gene, and a reporter plasmid that contains a second reporter gene. Although the preparation of such plasmids is now routine in the art, many appropriate plasmids are commercially available e.g., a plasmid with β-galactosidase is available from Stratagene.

The reporter plasmids can contain specific restriction sites in which an enhancer element having a strong STAT binding site or alternatively two tandemly arranged "weak" STAT binding sites can be inserted. In one particular embodiment, thirty-six hours after transfection of the cells with a plasmid encoding STAT-1, the cells are treated with 5 ng/ml interferon-γ Amgen for ten hours. Protein expression and tyrosine phosphorylation (to monitor STAT activation) can be determined by e.g., gel shift experiments with whole cell extracts.

Labels

Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents.

When a control marker is employed, the same or different labels may be used for the test and control marker gene.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419–439 (1980) and in U.S. Pat. No. 4,857,453.

Suitable enzymes include, but are not limited to, alkaline phosphatase, β-galactosidase, green fluorescent protein and its derivatives, luciferase, and horseradish peroxidase.

Other labels for use in the invention include magnetic beads or magnetic resonance imaging labels.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

Structure of the Amino-terminal Protein Interaction Domain of STAT-4

Summary

STATs are a family of transcription factors that are specifically triggered to participate in gene activation when cells encounter cytokines and growth factors. The crystal structure of a conserved domain comprising the first 123 residues of STAT-4 has been determined at 1.45 Å. This domain (N-terminal domain) has been implicated in several protein:protein interactions affecting transcription. The N-terminal domain enables STAT dimers to interact and to bind DNA cooperatively, a mechanism important for gene activation and binding site discrimination. The domain consists of 8 helices that are assembled into a hook-like structure. The crystal structure shows the formation of dimers formed by polar interactions across one face of the hook, revealing the nature of the cooperative interactions between STAT dimers. Mutagenesis of an invariant Trp residue that is at the heart of this interface abolishes cooperative dimer-:dimer DNA binding by the full length protein in vitro and reduces transcriptional response after cytokine stimulation in vivo.

Materials and Methods

Expression and purification of the STAT-4 N-terminal domain: The STAT-4 N-terminal domain was expressed as a C-terminal fusion with glutathione S-transferase (GST). The expression vector was constructed by PCR amplification (Vent DNA-polymerase, New England Biolabs) of the appropriate region of mouse STAT-4 cDNA and cloning of the fragment into the BamHI and EcoRI sites of pGEX2T (Pharmacia). Sequence comparison with the STAT-1 amino-terminal domain led to the decision to terminate the homologous domain in STAT-4 after residue 124. To facilitate cleavage of the GST tag from the recombinant STAT-4, three glycine residues were included after the thrombin cleavage site [Guan and Dixon, *Anal. Biochem.* 192:262 (1991)]. The resulting protein has four additional amino-terminal amino acids and Met 1 of STAT-4 is replaced with Gly. The construct was verified by dideoxy sequencing. BL21p(lysS) cells were grown and lysed as described [Vinkemeler et al., *EMBO J.* 15:5616 (1996)]. Soluble protein was incubated with 0.2 Vol. of a 50% (vol./vol.) slurry of glutathione agarose (Pharmacia). The bound protein was washed with cleavage buffer (50 mM Hepes/HCl pH 8.0, 150 mM KCl, 2.5 mM $CaCl_2$, 5 mM DTT). Cleavage with thrombin (~1 U/mg protein; Novagen) was performed overnight at room temperature with the protein bound to the beads. The eluted STAT-4 N-terminal domain fragment (in cleavage buffer) was concentrated to 20 mg/ml with centricon (Amicon) and used for crystallization.

Crystallization and data collection and processing: Initial studies were performed with the STAT-1 N-terminal domain, but led only to small, needle-like crystals. Hanging drops of one µl of the STAT-4 N-terminal domain fragment was mixed with equal volumes of reservoir buffer containing 0.2 M $Na^+CH_3COO^-$, 0.1 M Tris/HCL pH 8.0, 17% PEG4000. Hexagonal crystals (0.2×0.2×0.2 mm) were routinely grown overnight at 20° C. The crystals contain one molecule of the STAT-4 N-terminal domain in the asymmetric unit, and are in the space group $P6_522$ (a=79.51 Å, b=79.51 Å, c=84.68 Å). Crystals were cryo-protected in reservoir solution enriched in PEG to 20% and glycerol to 22.5% prior to flash freezing. Heavy atom derivatives were prepared by soaking crystals for 30 minutes in a saturated solution of parahydroxy-mercuribenzoic acid diluted 1:20 with the cryoprotective solution. Data for the native crystal were collected at the Brookhaven National Laboratory at beam line X25 using a MAR imaging plate detector system. A MAD experiment on a parahydroxy-mercuribenzoic acid derivitized crystal was performed at the Brookhaven National Laboratory on beam line X4A using Fuji imaging plates. Data processing and reduction were carried out with HKL, DENZO, and SCALEPACK (written by Z. Otwinowski and W. Minor).

Model building and refinement. Model building was performed using O [Jones et al., *Acta Crystallogr.* A47: 110–119 (1991)]. Bulk solvent correction and anisotropic B-factor scaling was applied during refinement using X-PLOR [Brünger, *X-PLOR* (Version 3.1) *Manual*, The Howard Hughes Medical Institute and Department of Molecular Biophysics and Biochemistry, Yale University, 260 Whitney Avenue, New Haven, Conn. 06511, (1992)]. The final refinement statistics are shown in Table 1. Of the five heterologous residues at the amino-terminus the first three residues (GlySerGly) as well as the C-terminal residue Gln 124 are not visible in the electron density map. No amino acids occupy disallowed regions of the Ramachandran plot and 95% fall into the most favored region.

Preparation, Expression, and Purification of the Mutated STAT-1α:

Mutated STAT-1α (Trp 37 to Ala) was expressed from pAcSG2 in baculovirus infected insect cells. PCR was used to exchange codon 37 [TGG] with [GCA] in the NcoI/SpeI fragment of human STAT-1 cDNA. Additionally, a 6-His tag was added to the C-terminus. Modifications were confirmed by sequencing. Insect cells were lysed (dounce homogenizer), mutated STAT-1α purified under native conditions on $Ni^{2+}$ nitrilotriacetic acid (Qiagen) and eluted with 200 mM imidazole in 20 mM Tris/HCl, pH 8.0, 10 mM $MgCl_2$, 50 mM KCl, 5 mM DTT.

Preparation of EGF-receptor kinase and in vitro phosphorylation of STAT proteins. Tyrosine phosphorylated wild type human STAT-1α was produced as described [Vinkemeier et al., *EMBO J.* 15:5616 (1996)]. In vitro phosphorylation was done as described [Vinkemeier et al., *EMBO J.* 15:5616 (1996)]. Human carcinoma A431 cells were grown to 90% confluency in 150 mm diameter plates in Dulbecco's modified Eagle's medium supplemented with 10% bovine calf serum (Hyclone). Cells were washed once with chilled PBS and lysates were prepared in 1 ml ice cold lysis buffer (10 mM Hepes/HCl, 150 mM NaCl, 0.5% Triton X-100, 10% Glycerol, 1 mM $Na_3VO_4$, 10 mM EDTA, Complete™ protease inhibitors, pH 7.5). After 10 min on ice, the cells were scraped, vortexed and dounce homogenized (5 strokes). The lysates were cleared by centrifugation at 4° C. for 20 min at top speed in an Eppendorf microfuge and stored at −70° C. until needed. Immediately before use 1 volume of the lysate was diluted with 4 volumes of the lysis buffer ("diluted lysate"). EGF-receptor precipitates were obtained by incubating 5 ml of diluted lysate with 50 µg of an anti-EGF-receptor monoclonal antibody directed against the extracellular domain. After 2 hours of rotating the sample at 4° C., 750 µl of Protein-A-agarose (50% slurry; Oncogene Science) was added, and the incubation was allowed to proceed, while rotating, for another 1 hour. Agarose beads containing the EGF-receptor immunoprecipitates were then washed 5 times with lysis buffer and finally twice with storage buffer (20% Glycerol, 20 mM Hepes/HCl, 100 mM NaCl, 0.1 mM $Na_3VO_4$). Precipitates from 5 ml diluted lysate were dissolved in 0.5 ml storage buffer, flash frozen on dry ice and stored at −70° C. Immediately before an in vitro kinase reaction the Protein-A-agarose bound EGF-receptor from 5 ml dilute lysate was washed once with 1× kinase buffer (20 mM Tris/HCl, 50 mM KCl, 0.3 mM $Na_3VO_4$, 2 mM DTT, pH 8.0) and then dissolved in 0.4 ml (total volume) of this buffer. Afterwards the washed EGF-receptor precipitate was incubated on ice for 10 min in the presence of a final concentration of mouse EGF of 0.15 ng/µl. Phosphorylation reactions were carried out in Eppendorf tubes in a final volume of 1 ml. To the pre-incubated kinase preparation the following was added: 60 µl 10× kinase buffer, 20 µl 0.1 M DTT, 50 µl 0.1 M ATP, 4 mg STAT protein (Superdex 200 eluate for STAT1α and STAT1 β; ammonium sulfate pellets dissolved in [20 mM Tris /HCl, pH 8.0] for STAT1tc), 10 µl 1M $MnCl_2$ and $dH_2O$ to 1 ml. The reaction was allowed to proceed for 15 hours at 4° C. After 3 hours an additional 15 µl of 0.1 M ATP was added.

Gel Shift Experiments and Determination of Tetramer Stability:

Gel shift experiments and determination of tetramer stability were done as described [Vinkemeier et al., *EMBO J.* 15:5616 (1996)] with an oligonucleotide containing two copies of the STAT recognition element from the c-fos gene [Wagner et al., *EMBO J.* 9:4477 (1990)] spaced by 10 base pairs (5'-GCCAGTCAGTTCCCGTCAATGCATCAGGTT-CCCGTCAATGCAT-3', SEQ ID NO:4). Both protein preparations (Tyr-phosphorylated wild type STAT-1α and W37A mutant) were titrated in gel shift experiments with an oligonucleotide containing a single M67 site (5'-GCCGATTTCCCGTAAATCAT-3', SEQ ID NO:5) [Wagner et al., *EMBO J.* 9:4477 (1990)] to assure similar loading of active protein. A 12.5 µl reaction volume contained DNA binding buffer (20 mM Hepes/HCl, 4% Ficoll, 40 mM KCl, 10 mM $MgCl_2$, 10 mM $CaCl_2$, 1 mM DTT) radiolabelled DNA at a final concentration of $1×10^{-10}$ M unless stated otherwise, 50 ng dIdC, 0.2 mg/ml BSA (Boehringer Mannheim), and the indicated amount of purified phosphorylated STAT protein. The reaction volume was mixed and then incubated at room temperature. The time necessary to reach equilibrium was assessed by EMSA [(Stone et al., in Jost, J. P. & Saluz, H. P. (eds.) *A Laboratory Guide to In Vitro Studies of Protein-DNA Interactions BioMethods*, vol.5:163–195 (1991)]. For all DNA fragments tested, equilibrium turned out to be fully established at the earliest timepoint that can be determined by this technique (30 sec). Therefore incubation periods of 5–15 minutes were chosen. Reaction products were loaded onto a 4% polyacrylamide gel (1.5 mm thick) containing 0.25×Tris-borate-EDTA which had been pre-run at 20 V/cm for 2 hours at 4° C. Electrophoresis was continued for 60 minutes at 4° C. Gels were dried and exposed to X-ray film and quantitated by a Molecular Dynamics Phospholmager.

Transient transfections: Transient transfections were performed on six well plates with 50% confluent U3A cells using the calcium phosphate method as instructed by the manufacturer (Stratagene) with the following modifications. Transfection reactions contained per well 4.5 µg of either wild type STAT-1α or the W37A mutant in plasmid pcDNA3 (Invitrogen), 4 µg luciferase reporter plasmid pLuc, and 0.4 µg β-galactosidase reporter plasmid (Stratagene). The luciferase reporter contained in its BamH1 site as an enhancer element two tandemly arranged "weak" STAT-1 binding sites (5'-GATCAGTTCCCGTCAATCA-TGATCCAGTTCCCGTCAATGATCCCCGGGATC-3', SEQ ID NO:6 binding sites underlined) from the human c-fos promoter. 36 hrs. after transfection, cells were treated with 5 ng/ml interferon-γ (Amgen) for 10 hrs. or left untreated. Luciferase assays were performed according to the manufacturer's protocol (Promega) and β-galactosidase assays were done as previously described [Ausubel et al., in *Current Protocols in Molecular Biology*, J. Wiley & Sons, Inc. (1994)]. Protein expression and Tyr-phosphorylation were checked in gel shift experiments with whole cell extracts for both wild type and mutant protein and were comparable. All results shown are luciferase activities normalized against the internal control β-galactosidase activity.

Results

Proteolytic digestion of purified STAT-1 showed that the N-terminal 131 residues form a stable domain that is readily cleaved off the intact molecule, indicating that it is an independently folded module [Vinkemeier et al., *EMBO J.* 15:5616 (1996)]. Sequence alignments show that the N-terminal domain is highly conserved in the STAT family of proteins (FIG. 1). The average sequence identity for this region between mammalian STAT proteins is 40%, and ranges from 51% between STAT-1 and STAT-4 to 20% between STAT-5 and STAT-6. Over the approximately 750 amino acids that span the length of the common core of the STATs only the SH2 domain is more highly conserved [Schindler and Darnell, *Annu. Rev. Biochem.* 64:621 (1995)]. The N-terminal domain is also found in the Drosophila STAT (dSTAT92E) [Hou et al., *Cell* 84:411 (1996); Yan et al., *Cell* 84:421 (1996)], (FIG. 1) and in the recently discovered STAT in Dictyostelium discoideum [Kawata et al., *Cell* 89:909 (1997)]. Interestingly, the first gene defect established in the DSTAT92 gene is a misspliced variant that produces both normal mRNA and an mRNA encoding only the N-terminal 41 residues. Expression of this fragment has a partial dominant negative effect on transcriptional activation by the wild type protein in cell culture. In the fly it is associated with a weak abnormal phenotype [Yan et al., *Proc. Natl. Acad. Sci. USA* 93:5842 (1996)].

As disclosed herein the crystal structure of the N-terminal domain of STAT-4 has been determined by multi-wavelength anomalous diffraction and refined at a resolution of 1.45 Å (R=19.4%, $R_{free}$=22.3%) (Table 1). The STAT-4 N-domain is all helical, with an unusual architecture. Instead of the up-down connectivity of helix bundles or the box-like helical packing of the globin fold, the N-domain is constructed from three distinct structural elements that pack together. The N-terminal 40 residues encompass the first 4 helices (α1–α4), which form a ring-shaped element (colored red in FIGS. 2 and 3B). A small helix (α5) connects this ring to the next structural element, an anti-parallel coiled-coil formed by helices α6 and α7. The heptad repeat of hydrophobic amino acids, characteristic of coiled-coils, is conserved across the STATs (FIG. 1). Finally, the distal surface of the ring-shaped element forms a docking site for the last helix in the structure (α8). The overall appearance of the structure is that of a triangular hook, with the inner surface of the hook being formed by the intersection of the proximal surfaces of the ring-shaped element and the coiled-coil. The N-domain of STAT-4 is dimeric in solution, and a two-fold symmetry axis in the crystal generates a dimer with an extensive polar interface that involves one face of the hook.

The N-domain (as depicted below with the amino acid numbering of SEQ ID NO:9) has a well defined hydrophobic core that is conserved across the STATs, consistent with a stable and defined fold (FIGS. 1 and 2). However, a notable feature of the N-terminal ring-shaped element is that it is stabilized by polar interactions involving buried charges. The ring is closed off by a helix-dipole interaction between the N-termninal region of helix α1 and the carboxylate group of Glu 39, presented by the C-terminal region of helix α4 (FIG. 2B). Glu 39 forms a hydrogen bond with the amide nitrogen of the Gln 3 residue, and is oriented correctly for this charge dipole interaction by the side chain of Arg 31, which in turn forms a buried ion pair with Glu 112. Glu 112 is positioned by interactions with Tyr 22 and a buried water molecule. Each of the side chains involved is invariant in all STATs (FIG. 1), indicating that the ring-shaped element is conserved in the STAT architecture.

TABLE 1

| | Summary of the Crystallographic Analysis | | | | | |
|---|---|---|---|---|---|---|
| | Resolution (Å) | Reflections total/unique | Completeness (%) | $R_{sym}$* (%) | $I_n/\sigma$† | Sites (N) | FOM# |
| Native Data MAD Analysis | 1.45 | 237647/27594 | 96.4 (91.7) | 7.2 (19.2) | 19.6 (4.2) | | |
| λ1 = 1.00542 Å | 2.15 | 112445/8554 | 95.6 (95.7) | 7.7 (21.2) | 24.7 (6.1) | 2 | |

TABLE 1-continued

| | | | | | | |
|---|---|---|---|---|---|---|
| λ2 = 1.01337 Å | 2.15 | 131403/5992 | 100.0 (100.0) | 7.3 (21.1) | 27.2 (5.1) | 2 |
| λ3 = 1.00932 Å | 2.00 | 126292/10731 | 96.6 (95.7) | 5.4 (33.4) | 22.1 (4.5) | 2 |
| | | | | | | 0.542 |

| Refinement | Cut Off | Reflections | Completeness (%) | R-factor (%)¶ | R-free (%)‡ |
|---|---|---|---|---|---|
| 10–1.45 Å | \|F\|/σ(\|F\|) > 2 | 25255 | 88.8 | 18.8 | 21.6 |
| 10–1.45 Å | all data | 26560 | 93.3 | 19.4 | 22.3 | r.m.s. deviation of model

| | |
|---|---|
| bond lengths (Å) | 0.015 |
| bond angles (degrees) | 1.4 |
| average B-factor (protein) (Å$^2$) | 9.6 |
| water molecules | 165 |
| average B-factor (water) (Å$^2$) | 25 |

\*$R_{sym} = 100 \times \Sigma_n\Sigma_i I_{h,i} - I_h|/\Sigma_h\Sigma_i I_{h,i}$ for the intensity I of i observations of reflection h. For $R_{sym}$ and completeness, the numbers in parenthesis refer to data in the shell of highest resolution. $I_n$ is the mean intensity of the reflection.
†$I_n/\sigma$ = mean intensity/mean standard deviation.
FOM = overall mean figure of merit [$|\Sigma P(\alpha)e^{i\alpha}/\Sigma P(\alpha)|$], where α is the phase and P(α) is the phase distribution probability.
¶R-factor = $100 \times \Sigma|F_{obs} - F_{calc}|/\Sigma|F_{obs}|$, where $F_{obs}$ and $F_{calc}$ are the observed and calculated structure factors, respectively.
‡R-free = is the same as R-factor, but calculated on the 5% of the reflection data excluded from refinement.

TABLE II

Interactions Between the Two N-terminal Domains of Stat4 (SEQ ID NO:9)

sidechain-sidechain contacts; direct

| Molecule A | Å | Molecule B |
|---|---|---|
| Asn5 | 3.0 | Asn5 |
| Trp37 | 3.2 | Glu66 |
| Thr40 | 3.2 | Arg70 |
| | 3.2 | Gln67 |
| Gln41 | 2.9 | Glu66 |
| Asp42 | 3.3 | Lys73 |
| Gln63 | 3.6 | Gln63 |
| Glu66 | 3.2 | Trp37 |
| Gln67 | 3.2 | Thr40 |
| Arg70 | 3.0 | Thr40 |
| Lys73 | 3.3 | Asp42 | sidechain-sidechain contacts; water mediated

| Molecule A | Å | Water A | Å | Water B | Å | Water C | Å | Molecule B |
|---|---|---|---|---|---|---|---|---|
| Gln36 | 3.0 | H$_2$O 984 | 2.9 | H$_2$O 269 | | | 2.7 | Glu39 |
| Trp37 | 3.1 | H$_2$O 167 | | | | | 3.0 | Gln63 |
| Glu39 | 2.8 | H$_2$O 186 | | | | | 3.4 | Arg70 |
| | 2.7 | H$_2$O 269 | | | | | 2.8 | Arg70 |
| Thr40 | 2.8 | H$_2$O 314 | | | | | 2.8 | Gln67 |
| | 2.8 | H$_2$O 314 | 2.8 | H$_2$O 6 | 2.8 | H$_2$O 314 | 2.8 | Thr40 |
| | | | | | | | 2.8 | Glu66 |
| Gln41 | 2.8 | H$_2$O 5212 | | | | | 2.9 | Glu66 |
| Asn59 | 2.9 | H$_2$O 212 | | | | | 2.9 | Glu66 |
| Gln63 | 2.7 | H$_2$O 901 | | | | | 2.7 | Gln63 |
| | 3.0 | H$_2$O 164 | | | | | 3.1 | Trp37 |
| Glu66 | 2.7 | H$_2$O 164 | | | | | 3.1 | Trp37 |
| | 2.8 | H$_2$O 6 | 2.8 | H$_2$O 314 | | | 2.8 | Thr40 |
| | 2.9 | H$_2$O 212 | | | | | 2.9 | Asn59 |
| | | | | | | | 2.8 | Gln41 |
| Gln67 | 3.2 | H$_2$O 6 | 2.8 | H$_2$O 314 | | | 2.8 | Thr40 |
| Arg70 | 2.8 | H$_2$O 314 | | | | | 2.8 | Thr40 |
| | 3.4 | H$_2$O 186 | | | | | 2.8 | Glu39 |
| | 3.1 | H$_2$O 269 | | | | | 2.7 | Glu39 |

TABLE II-continued

Interactions Between the Two N-terminal Domains of Stat4 (SEQ ID NO:9)

sidechain-mainchain contacts; direct

| Molecule A | Å | Molecule B |
|---|---|---|
| Gln36-N | 2.9 | Gln36 |
| Glu39-O | 3.6 | Arg70 |
| Arg70 | 2.6 | Glu39-O | sidechain-mainchain contacts; water mediated

| Molecule A | Å | Water A | Å | Water B | Å | Molecule B |
|---|---|---|---|---|---|---|
| His32-O | 2.9 | H$_2$O 1024 | | | 3.1 | Gln36 |
| Gln36-N | 3.2 | H$_2$O 41 | | | 2.7 | Gln36 |
| Gln36 | 3.1 | H$_2$O 1024 | | | 2.9 | His31-O |
| Trp37-N | 2.9 | H$_2$O 41 | | | 2.7 | Gln36 |
| Glu66-O | 2.7 | H$_2$O 5107 | 2.8 | H$_2$O 5078 | 2.7 | Gln41 |

The distance in Ångstroms (Å) between the interacting amino acid residues and/or molecules are provided. The water molecules are numbered according to their structure file. The mainchain contacts are indicated by "-N" or "-O" for backbone amido or carboxyl groups respectively.

A consequence of the utilization of these polar groups in the ring-shaped element is the formation of a compact and potentially specific interaction surface. This structural element forms a relatively flat molecular surface that packs at an angle against another surface presented by the coiled-coil formed by helices α6 and α7. The juxta positioning of the surface of the ring-shaped element with that of the coiled-coil results in a wedge-shaped groove. This groove is lined with hydrophobic residues, with polar residues at the center, and has the natural appearance of a ligand binding site. A possible function for this groove is suggested by the fact that replacement of Arg 31 or Glu 39 in STAT-1 (SEQ ID NO:1) by Ala results in a molecule that is much slower to dephosphorylate after interferon-γ induction when compared to wild type protein [Shuai et al., *Mol. Cell. Biol.* 16:4932 (1996)]. Mutation of these two residues is likely to drastically alter the conformation of the ring-shaped element (FIG. 2B), suggesting that a phosphatase that controls STAT dephosphorylation might bind to the groove in the N-terminal domain.

Figure 3A:
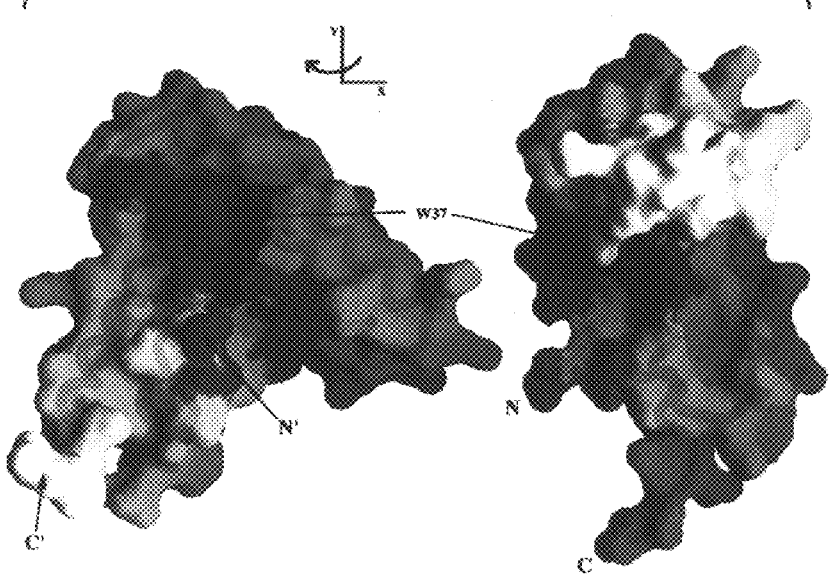
FIG. 3A depicts the surface representation of the N-terminal domain indicating the wedge shaped groove and the dimerization interface. Shown are two monomers of a dimer with the left one rotated 90° around the vertical axis away from the original position in the dimer. Note the hook-like appearance of the monomer with the coiled-coil of helices α6 and α7 pointing out of the planar surface formed by the ring-shaped element comprising the amino-terminal 40 residues. Residues from three separate regions of the N-terminal domain make direct or water mediated contacts in the dimer and are color-coded according to their position. Interface residues at the amino-terminus are in green, those in helices α3 and α4 are in blue and amino acids located in helix α6 are yellow. The position of the critical Trp 37 is highlighted in red. The Figure was created using GRASP [Nicholls et al., *Proteins: Struct. Funct. and Genetics* 11:281 (1991)].
Figure 3B:
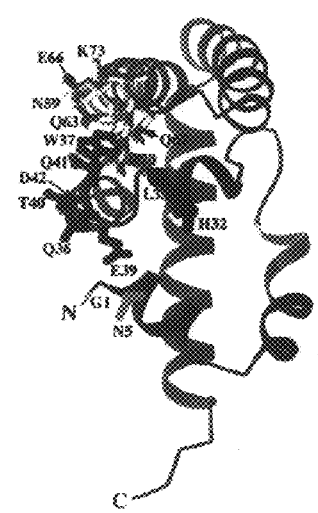
Figure 3C:
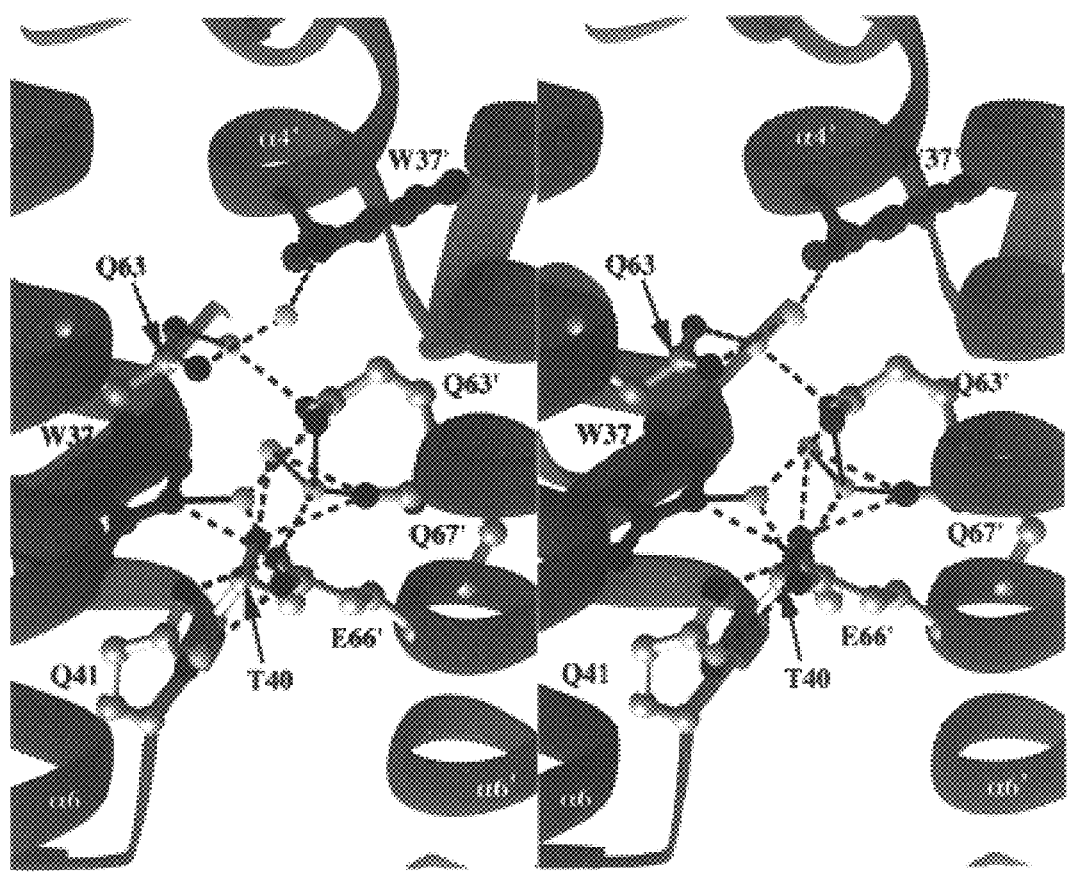

There is one molecule in the asymmetric unit of the STAT-4 crystal, and it is related to another by a two-fold symmetry axis (FIG. 2A and 3A). There is an extensive interface between the two monomers of the dimer, burying 1,714 $Å^2$ of surface area (FIG. 3A). An extended intermolecular hydrogen bonding network is formed at the interface, involving 15 amino acid side chains and 12 water molecules per monomer (FIG. 3B). In addition 5 backbone contacts are also observed in each monomer. 11 of the 15 residues at the interface make direct hydrogen bonding contacts to the other monomer. The water molecules at the interface are very well defined in the electron density map, many of them having low temperature factors (<10 $Å^2$) (FIG. 3C).

Figure 1B:
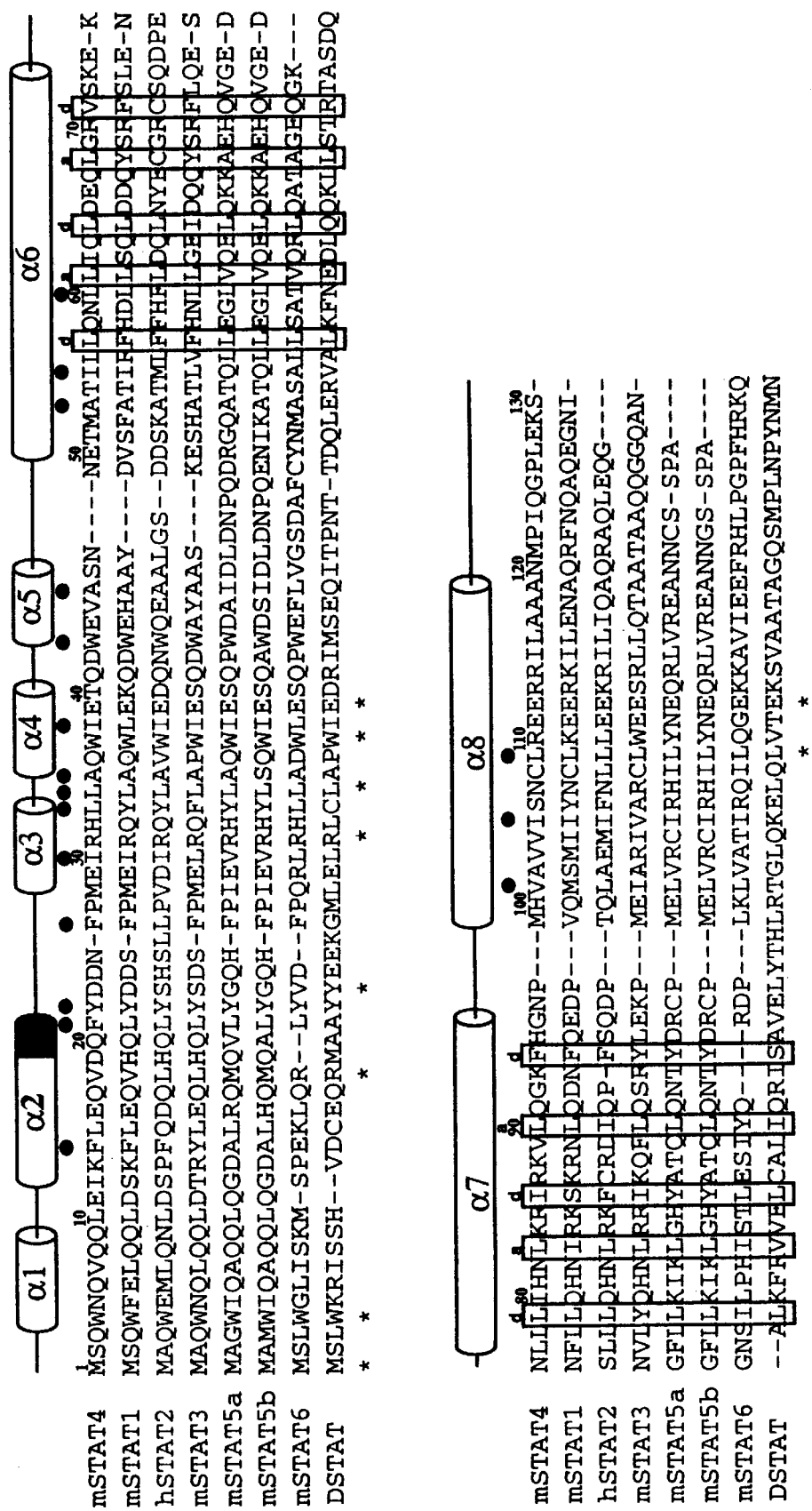
FIG. 1B shows the sequence alignment of the conserved N-terminal domain of the STAT family and secondary structure of the N-terminal domain of STAT-4, and the following sequences are shown: mSTAT4 (SEQ ID NO:9), mSTAT1 (SEQ ID NO:7), hSTAT2 (SEQ ID NO:2), mSTAT3 (SEQ ID NO:8), mSTAT5a (SEQ ID NO:10), mSTAT5b (SEQ ID NO:11), mSTAT6 (SEQ ID NO:12), dSTAT (SEQ ID NO:13), Human (hSTAT), murine (mSTAT), and Drosophila (DSTAT) proteins are included. The numbering is according to STAT-4. α-Helices α1 to α8 are drawn as cylinders. The blackened part of helix α2 indicates a $3_{10}$ helix. Invariant residues are highlighted with an asterisk below the alignment. Conserved residues in the hydrophobic core are marked with filled circles above the STAT-4 sequence. The following amino acid exchanges are considered conserved: Q/N, D/E, I/L/V, R/K/H, Y/F, S/T. Residues in helices α6 and α7 that contribute to the packing of the coiled-coil are boxed and their position in the helical repeats is indicated (a or d).

The interface is almost entirely polar, with no involvement of hydrophobic side chains. In contrast to the leucine zipper, wherein hydrophobic residues are utilized to generate the intermolecular interface by the formation of a coiled-coil across the dimer interface [Lupas, *Trends in Biochemical Sciences* 21:375 (1996)], the coiled-coil in the N-terminal domain is firmly anchored within one N-terminal domain and its role is to serve as an architectural support for the presentation of a number of interacting side chains at the dimer interface and at the potential interaction groove. While hydrophobic interactions are associated with stabilization of folded protein structures and are often found at the core of tight interfaces, polar interactions can provide both stability and specificity in protein-protein interactions [Fersht et al., *Nature* 314:235 (1985); Xu et al., *Journal of Molecular Biology* 265:68 (1997)]. In contrast to the residues that constitute the buried core of the N-terminal domain, which are conserved across STATs, the majority of the residues at the dimer interface are not conserved (FIG. 1 and 3B). This variation could provide specificity in STAT dimer:dimer interactions on DNA. Only two of the residues at the interface are invariant in all STATs (SEQ ID NOs:2 and 7–13, and FIG. 1B) Trp 37, a central anchor residue at the interface, and Glu 39, which also participates in the formation of the ring-shaped element.

To test the physiological relevance of the dimer that is observed in the crystal structure it was determined if the mutation of the critical Trp 37 residue at the interface would disrupt or reduce oligomerization in vitro and transcriptional activation in vivo. These experiments were carried out using STAT-1, for which a DNA-protein interaction assay had been worked out previously [Vinkemeier et al., *EMBO J*. 15:5616 (1996)]. In addition, a cell line (U3A) lacking STAT-1 is available [Müller et al., *EMBO J*. 12:4221 (1993)] allowing the introduction of expression vectors encoding mutant STAT-1 molecules. The close similarity between the N-terminal domains of STAT-1 and STAT-4 (51% amino acid identity) ensures that the structural information derived from the STAT-4 crystal structure is an accurate representation of the STAT-1 architecture.

Conditions under which an oligonucleotide bearing tandem binding sites binds full length STAT-1 as a tetramer have been established; the site contains two "weak" binding sites, spaced 10 base pairs apart [Vinkemeier et al., *EMBO J*. 15:5616 (1996)]. Competition experiments show that the off time is long for wild type STAT-1 (greater than 15–30 minutes), indicating the formation of a stable complex. In contrast, if an oligonucleotide containing only one "weak" site is used instead, the off time was less than 30 seconds [Vinkemeier et al., *EMBO J*. 15:5616 (1996)]. The stabilization of STAT-1 on oligonucleotides containing tandem binding sites is not observed if the N-terminal domain is deleted [Vinkemeier et al., *EMBO J*. 15:5616 (1996)]. This assay was used to test the DNA binding properties of STAT-1 in which Trp 37 was replaced by Ala (W37A). Trp 37 plays a central role at the dimer interface, and participates in both direct and water mediated interactions with the other monomer (FIG. 3C).

Figure 4A:
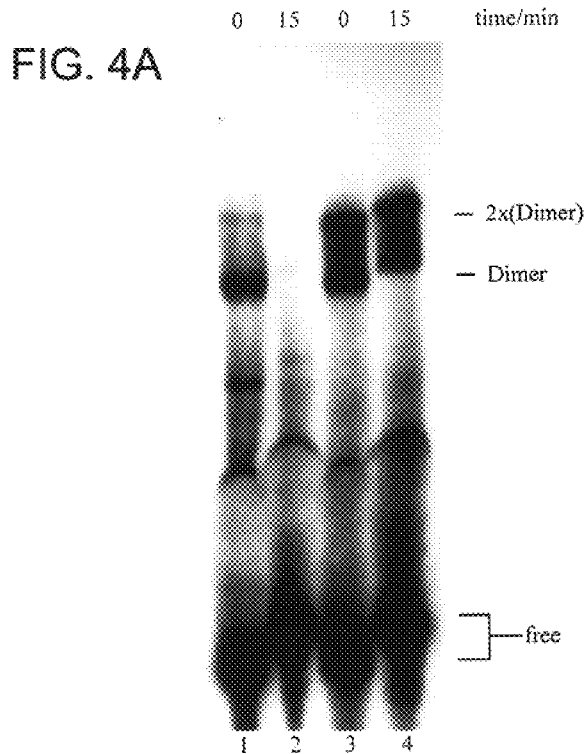
FIG. 4A depicts the gel mobility shift that shows that a single point mutation disrupts STAT-1 cooperative DNA-binding. Comparison of tetramer stability between wild type (WT) STAT-1 (lanes 3 and 4) and the W37A mutant (lanes 1 and 2). Radiolabeled DNA containing a tandem binding site was preincubated with equal amounts of active protein of either tyrosine-phosphorylated WT-STAT or the mutant protein followed by a chase with excess (30 fold) unlabeled oligonucleotide for the indicated amount of time. The wild type STAT-1 shows the expected formation and stabilization of 2× (dimeric) complexes relative to the dimeric protein/DNA complex. The W37A mutant does form dimeric complexes, but only very little of the slower migrating 2× (dimeric) species. No increased stability of the 2× (dimeric) complex relative to the dimer is observed. Samples loaded at the later time point (15 minutes) were electrophoresed for shorter times and therefore run higher on the gel. The position of unbound oligonucleotide is marked (free).
Figure 4B:
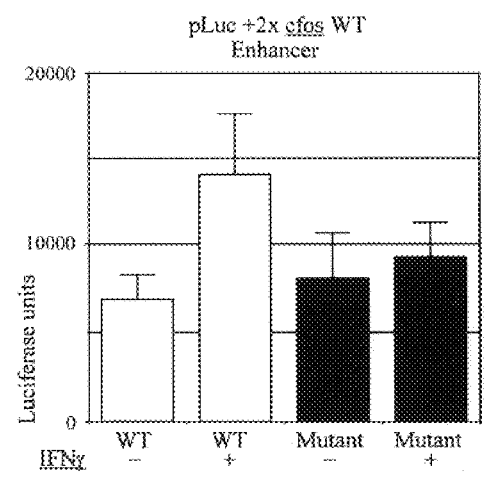
FIG. 4B show the effect of STAT-1 W37A mutation on interferon-γ (IFN-γ) stimulated gene activation in vivo. U3A cells that are lacking STAT-1 [Müller et al., *EMBO J.* 12:4221 (1993)] were transfected with expression clones containing either wild type or mutant STAT-1 (see Methods of the EXAMPLE, below) along with a luciferase reporter containing a tandem STAT binding site as an enhancer. After stimulation with IFN-γ for 10 hours, luciferase expression was determined spectroscopically (represented as bars). Cells transfected with the wild type protein show an about 2-fold increase in luciferase expression. In contrast, the tetramerization deficient W37A mutant does not markedly increase transcription over background levels from an enhancer with a tandem binding site. Each bar represents ten individual parallel experiments. Error bars denote standard deviation from the mean.

The W37A mutant protein binds to the DNA probe with tandem sites, but the interaction is completely displaced by the addition of unlabelled oligonucleotides (FIG. 4A). In contrast, the wild-type protein is resistant to displacement for more than 15 minutes. The same two tandem "weak" binding sites were used to drive transcription from a reporter gene in an interferon-dependent transcriptional assay. U3A cells were co-transfected with the reporter gene and with either wild type or W37A mutant STAT-1. The rather weak transcriptional induction by interferon γ (approximately 2-fold) was abolished by the mutation (FIG. 4B).

Activated and dimeric STAT proteins do not form detectable tetrameters in solution in the absence of DNA. It is not known whether this is a consequence of limited binding affinity between N-terminal domains or whether the conformation of the STAT molecule in the absence of DNA impedes further oligomerization. In any case, the presentation of highly polar and unique interaction surfaces by the N-terminal domains of the STATs provides a ready means for generating very specific interactions between adjacent STAT dimers on the DNA, since the hydrogen bonding constraints of the interacting groups places stereochemical constraints on potential partners. While each N-domain dimer is closed, the fact that each STAT dimer presents two N-domains for interaction makes possible the generation of open ended STAT-STAT interactions that are limited only by the nature and number of the adjacent DNA binding sites.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties. The citation of any reference herein should not be construed as an admission that such reference is available as "Prior Art" to the instant application.

What is claimed is:

1. A crystal of an N-terminal fragment of a Signal Transducer and Activator of Transcription (STAT) that effectively diffracts X-rays for the determination of the atomic coordinates of the N-terminal fragment of STAT to a resolution of better than 5.0 Angstroms; wherein the N-terminal fragment of the STAT protein consists of 122 to 128 amino acid residues and comprises a peptic consisting of amino acid residues 2–123 of SEQ ID NO:9; and wherein said crystal has a space group of P6$_5$22 with unit cell dimensions of a=79.51 Å, b=79.51 Å, and c=84.68 Å.

2. The crystal of claim 1 wherein said peptide further comprises SEQ ID NO:3; and wherein SEQ ID NO:3 is covalently attached to the N-terminal amino acid of said peptide.

3. The crystal of claim 2 wherein said peptide further comprises amino acid residue 124 of SEQ ID NO:9.

4. The crystal of claim 1 wherein said peptide further comprises amino acid residue 124 of SEQ ID NO:9.

5. A method of growing a crystal of the N-terminal fragment of a STAT of claim 1 in a solution, said method comprising growing a crystal of the N-terminal fragment by vapor diffusion using a reservoir buffer containing 0.2 M Na$^+$CH$_3$COO$^-$, 0.1 M Tris/HCL pH 8.0, and 17% PEG4000; wherein said solution comprises a 1:1 mixture of the reservoir buffer with the N-terminal fragment in 50 mM Hepes/HCl pH 8.0, 150 mM KCl, 2.5 mM CaCl$_2$, and 5 mM DTT.

* * * * *

UNITED STATES PATENT AND TRADEMARK OFFICE
CERTIFICATE OF CORRECTION

PATENT NO. : 6,087,473
DATED : July 11, 2000
INVENTOR(S) : Uwe Vinkemeier et al.

It is certified that error appears in the above-identified patent and that said Letters Patent is hereby corrected as shown below:

In the Claims in Claim 1, line 7:

Please replace the word "peptic" with

--peptide--.

Signed and Sealed this

Seventeenth Day of April, 2001

NICHOLAS P. GODICI

*Attest:*

*Attesting Officer*     *Acting Director of the United States Patent and Trademark Office*